(12) United States Patent
Desai et al.

(10) Patent No.: US 11,484,684 B2
(45) Date of Patent: *Nov. 1, 2022

(54) SYSTEM AND METHOD FOR ANESTHETIZING EUSTACHIAN TUBE

(71) Applicant: Acclarent, Inc., Irvine, CA (US)

(72) Inventors: Siddhi K. Desai, San Jose, CA (US);
Hung V. Ha, San Jose, CA (US);
Ketan P. Muni, San Jose, CA (US);
Randy S. Chan, San Jose, CA (US);
Andy Nguyen, San Jose, CA (US);
Mina W. Chow, Campbell, CA (US);
Mei Pader, Fremont, CA (US)

(73) Assignee: Acclarent, Inc., Irvine, CA (US)

( * ) Notice: Subject to any disclaimer, the term of this patent is extended or adjusted under 35 U.S.C. 154(b) by 818 days.

This patent is subject to a terminal disclaimer.

(21) Appl. No.: 16/134,358

(22) Filed: Sep. 18, 2018

(65) Prior Publication Data

US 2019/0083738 A1 Mar. 21, 2019

Related U.S. Application Data

(63) Continuation of application No. 14/928,423, filed on Oct. 30, 2015, now Pat. No. 10,118,012.

(51) Int. Cl.
*A61M 19/00* (2006.01)
*A61M 25/06* (2006.01)
(Continued)

(52) U.S. Cl.
CPC ............ *A61M 19/00* (2013.01); *A61F 11/20* (2022.01); *A61F 11/202* (2022.01);
(Continued)

(58) Field of Classification Search
None
See application file for complete search history.

(56) References Cited

U.S. PATENT DOCUMENTS 3,292,625 A * 12/1966 Marsan ................... A61F 5/442
604/334
4,366,817 A 1/1983 Thomas
(Continued)

FOREIGN PATENT DOCUMENTS

CN 203029796 U 7/2013
CN 103536395 A 1/2014
(Continued)

OTHER PUBLICATIONS

International Search Report and Written Opinion dated Feb. 6, 2017 for Application No. PCT/US2016/058731, 12 pgs.
(Continued)

*Primary Examiner* — Manuel A Mendez
(74) *Attorney, Agent, or Firm* — Frost Brown Todd LLC

(57) ABSTRACT

A system for delivering a fluid to a Eustachian tube (ET) of a patient includes a guide member and a tubular member. The guide member includes a shaft having a proximal portion, a distal portion, and a bend at the distal portion. The bend is configured to provide access to an opening in the ET. The system further includes a tubular member comprising a proximal end, a distal end, and a lumen extending therebetween. The tubular member is sized to fit within the ET. One or both of the tubular member and the guide member comprises a first stop member configured to engage the other of the tubular member or the guide member. The first stop member is configured to restrict a distal advancement of the tubular member relative to the guide member.

20 Claims, 17 Drawing Sheets

(51) Int. Cl.
- *A61M 25/10* (2013.01)
- *A61M 29/00* (2006.01)
- *A61M 31/00* (2006.01)
- *A61M 25/00* (2006.01)
- *A61M 29/02* (2006.01)
- *A61F 11/20* (2022.01)
- *A61B 17/24* (2006.01)
- *A61B 17/00* (2006.01)
- *A61B 1/00* (2006.01)
- *A61B 17/34* (2006.01)
- *A61M 25/01* (2006.01)
- *A61B 90/00* (2016.01)

(52) U.S. Cl.
CPC .... *A61M 25/0032* (2013.01); *A61M 25/0068* (2013.01); *A61M 25/0097* (2013.01); *A61M 25/0662* (2013.01); *A61M 25/10* (2013.01); *A61M 29/00* (2013.01); *A61M 29/02* (2013.01); *A61M 31/00* (2013.01); *A61B 1/00* (2013.01); *A61B 17/24* (2013.01); *A61B 17/3478* (2013.01); *A61B 2017/00331* (2013.01); *A61B 2017/00787* (2013.01); *A61B 2090/034* (2016.02); *A61B 2217/007* (2013.01); *A61M 25/0023* (2013.01); *A61M 25/0041* (2013.01); *A61M 25/0054* (2013.01); *A61M 2025/0036* (2013.01); *A61M 2025/0042* (2013.01); *A61M 2025/0073* (2013.01); *A61M 2025/0175* (2013.01); *A61M 2025/1095* (2013.01); *A61M 2210/0675* (2013.01)

(56) References Cited

U.S. PATENT DOCUMENTS

| | | |
|---|---|---|
| 4,884,573 A | 12/1989 | Wijay et al. |
| 5,531,719 A | 7/1996 | Takahashi |
| 5,573,520 A | 11/1996 | Schwartz et al. |
| 6,716,813 B2 | 4/2004 | Lim et al. |
| 9,399,121 B2 | 7/2016 | Goldfarb et al. |
| 10,118,012 B2* | 11/2018 | Desai ................ A61M 25/0032 |
| 2002/0173770 A1 | 11/2002 | Flory et al. |
| 2005/0085769 A1* | 4/2005 | MacMahon ......... A61M 25/007 |
| | | 604/96.01 |
| 2007/0264310 A1* | 11/2007 | Hissong ............... A61K 9/0046 |
| | | 424/437 |
| 2009/0299452 A1 | 12/2009 | Eidenschink et al. |
| 2010/0030031 A1 | 2/2010 | Goldfarb et al. |
| 2010/0030187 A1* | 2/2010 | Xia ....................... A61M 11/00 |
| | | 604/514 |
| 2010/0274188 A1 | 10/2010 | Chang et al. |
| 2013/0274715 A1 | 10/2013 | Chan et al. |
| 2015/0374963 A1 | 12/2015 | Chan et al. |

FOREIGN PATENT DOCUMENTS

| | | |
|---|---|---|
| CN | 203898818 U | 10/2014 |
| CN | 104288848 A | 1/2015 |

OTHER PUBLICATIONS

St. Croix, B., et al. "Genes Expressed in Human Tumor Endothelium," Science, Aug. 18, 2000, 289:1197-1202, 6pgs.
U.S. Appl. No. 62/139,919, filed Mar. 30, 2015.
Chinese Office Action and Search Report dated Aug. 5, 2019, for Application No. 201680063723.3, 10 pages.

\* cited by examiner

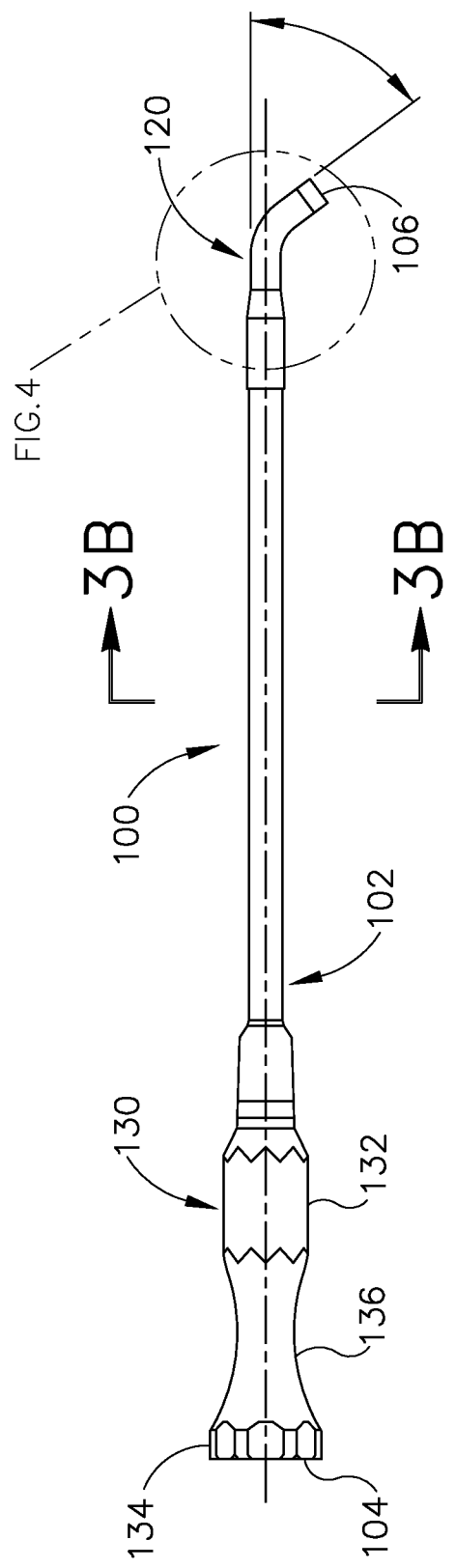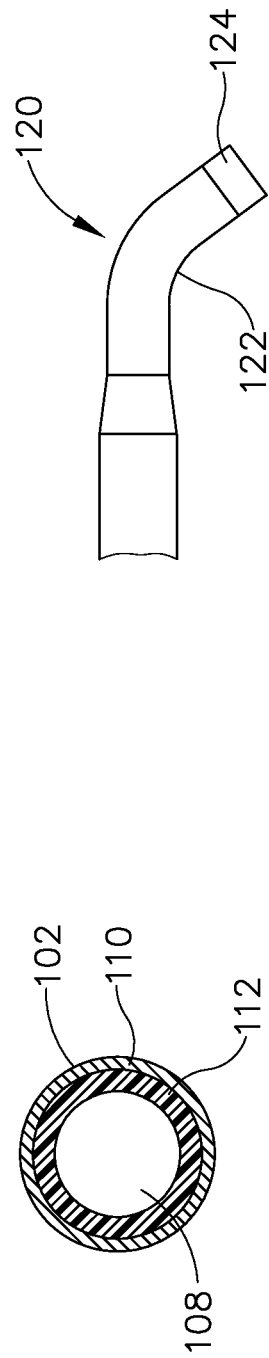

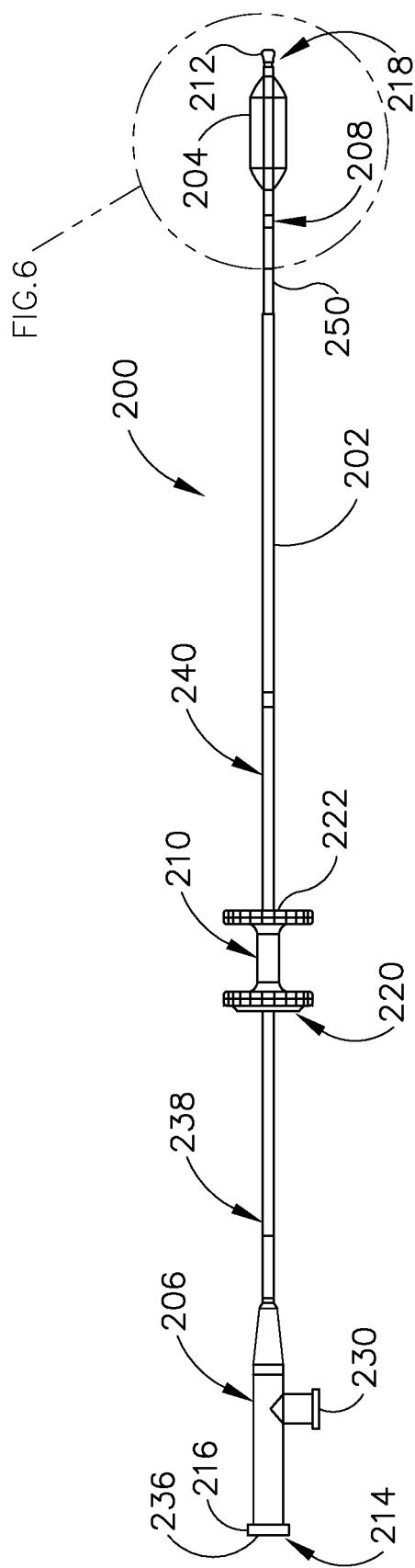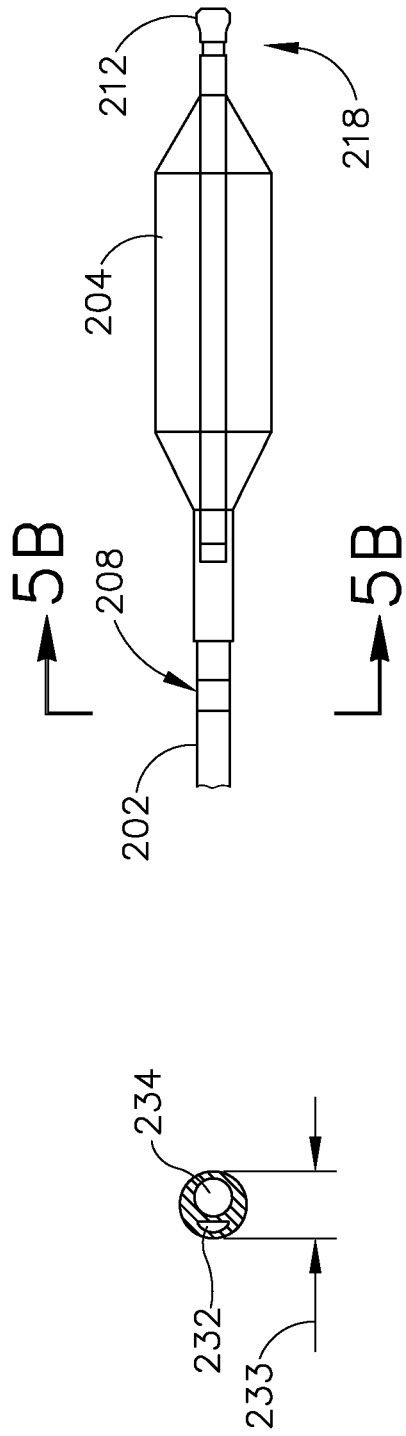
Fig.5A
Fig.5B
Fig.6

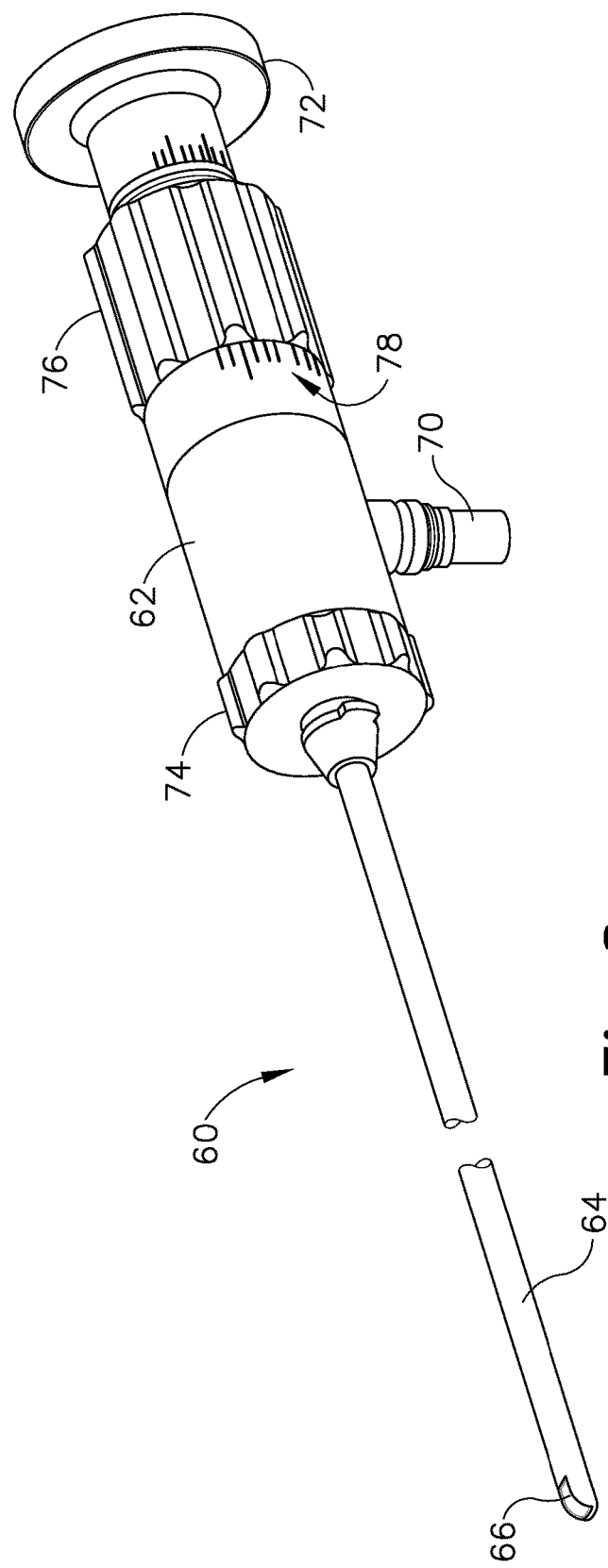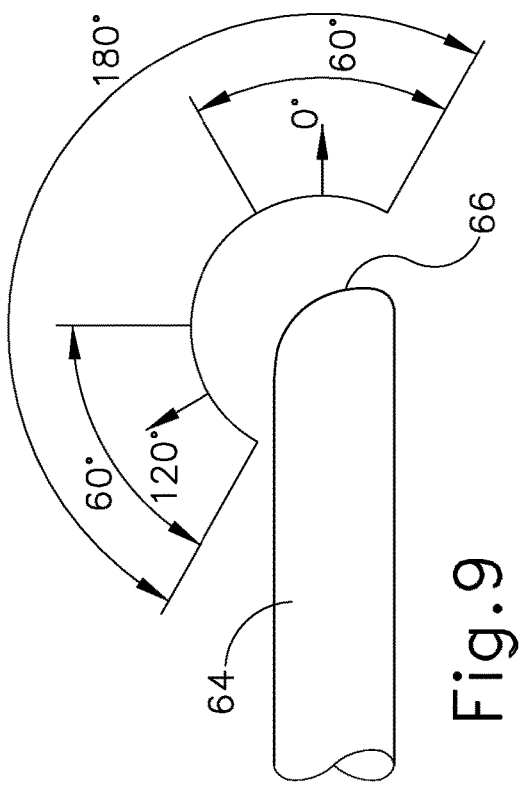
Fig.8
Fig.9

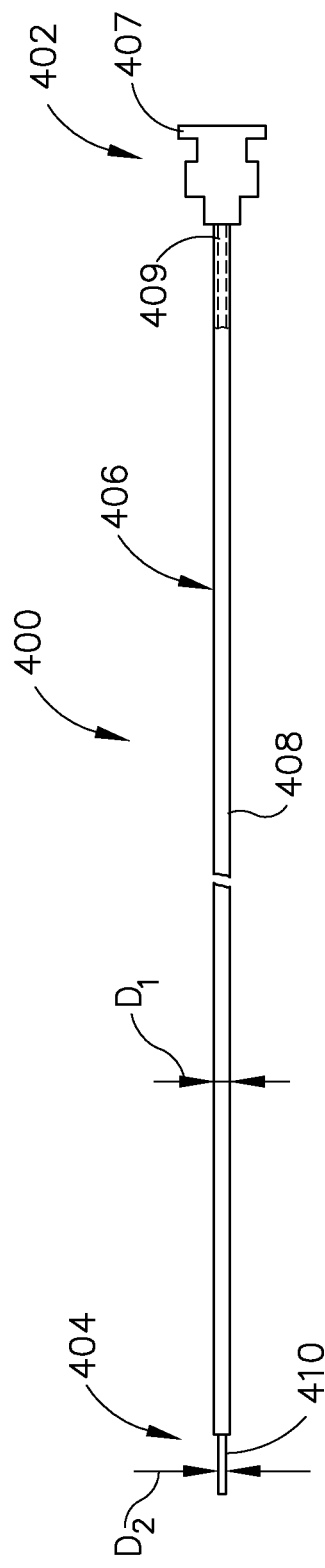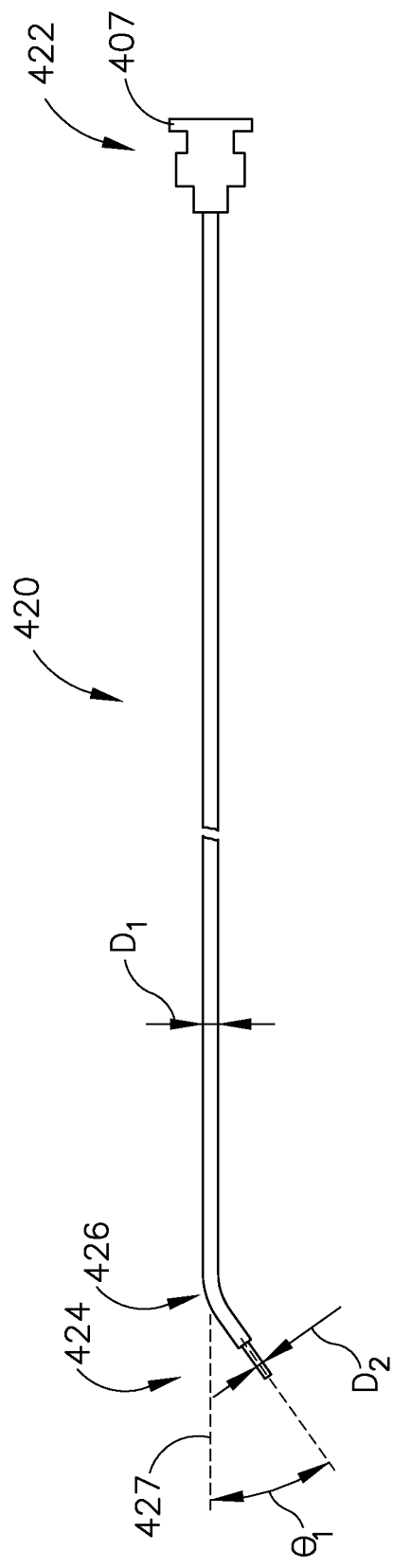

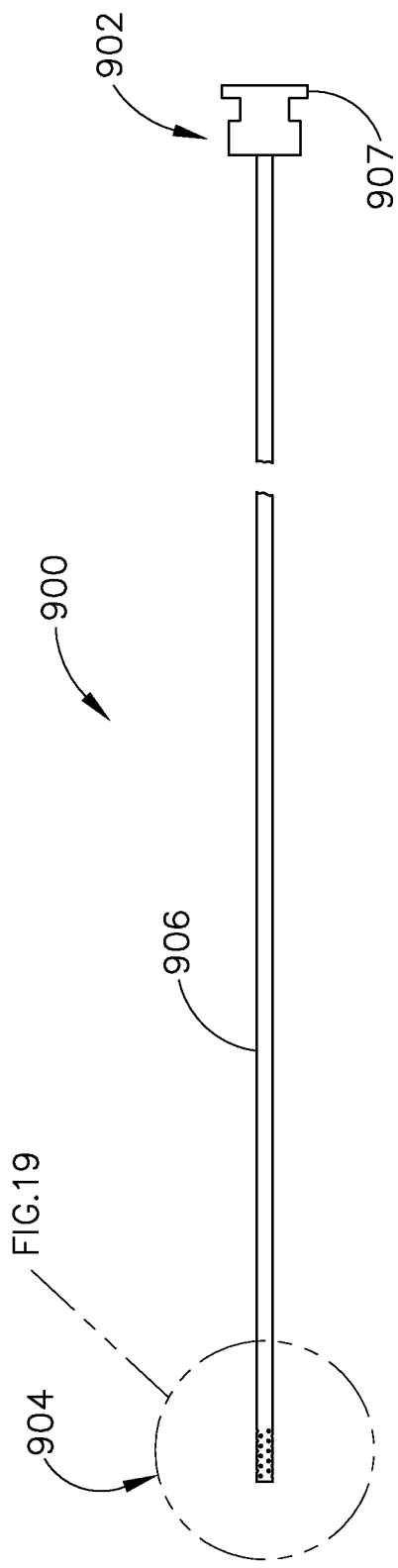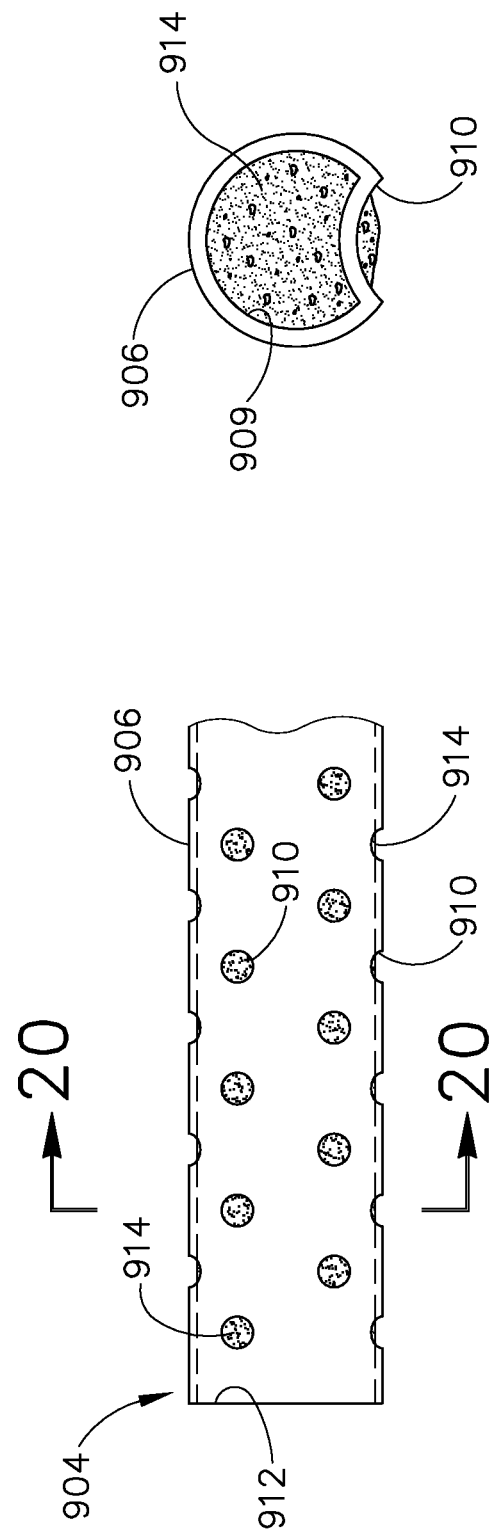

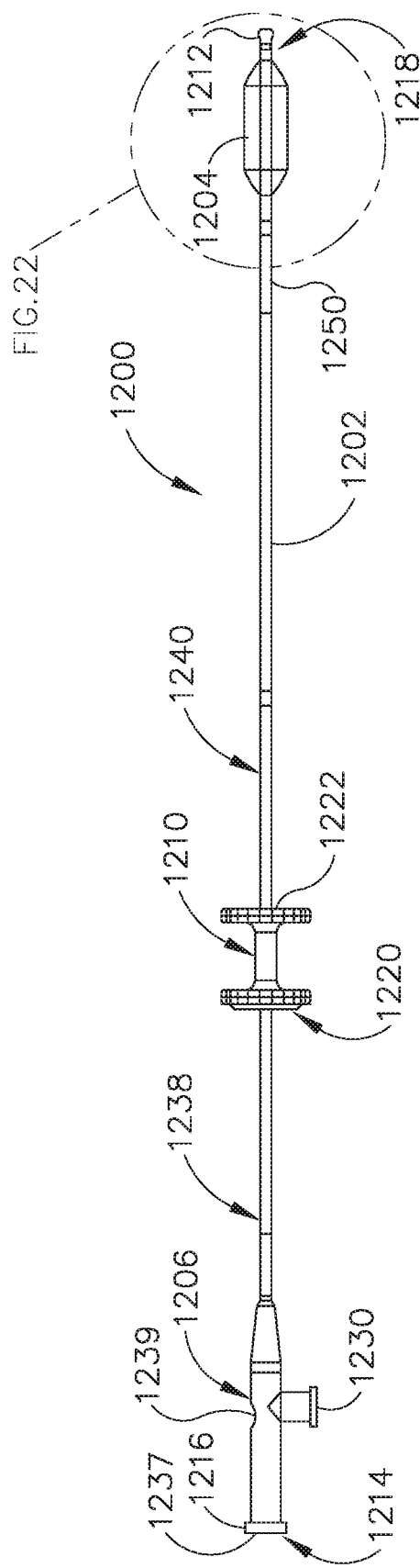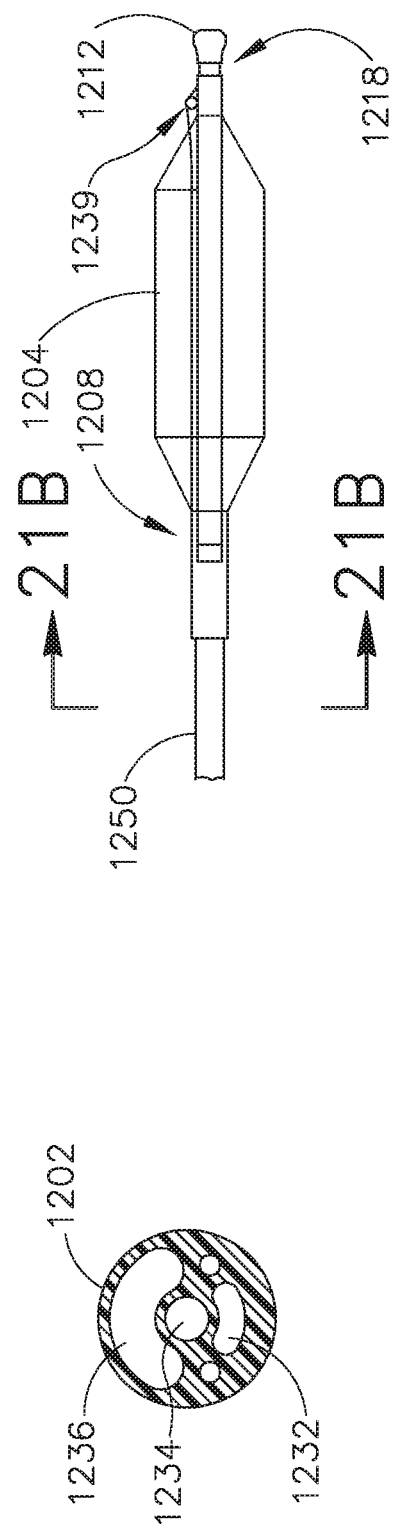

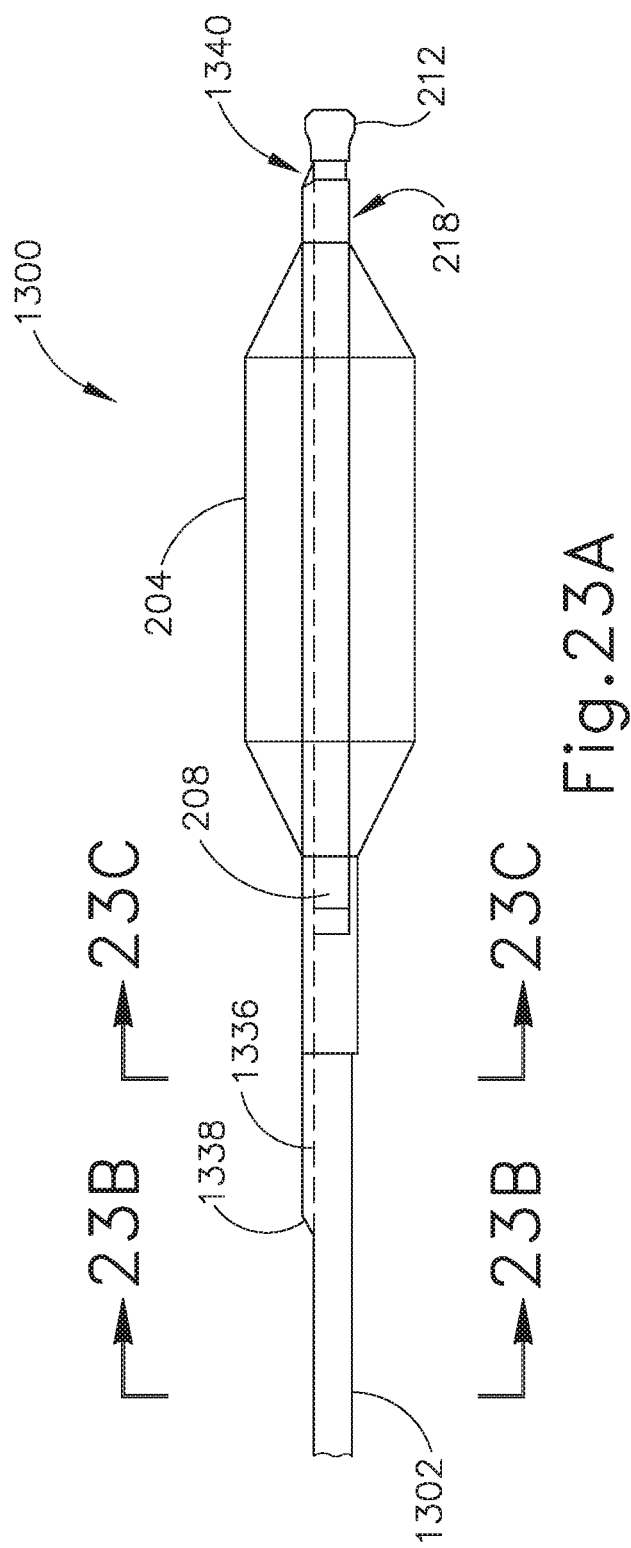
Fig.23A
Fig.23B
Fig.23C

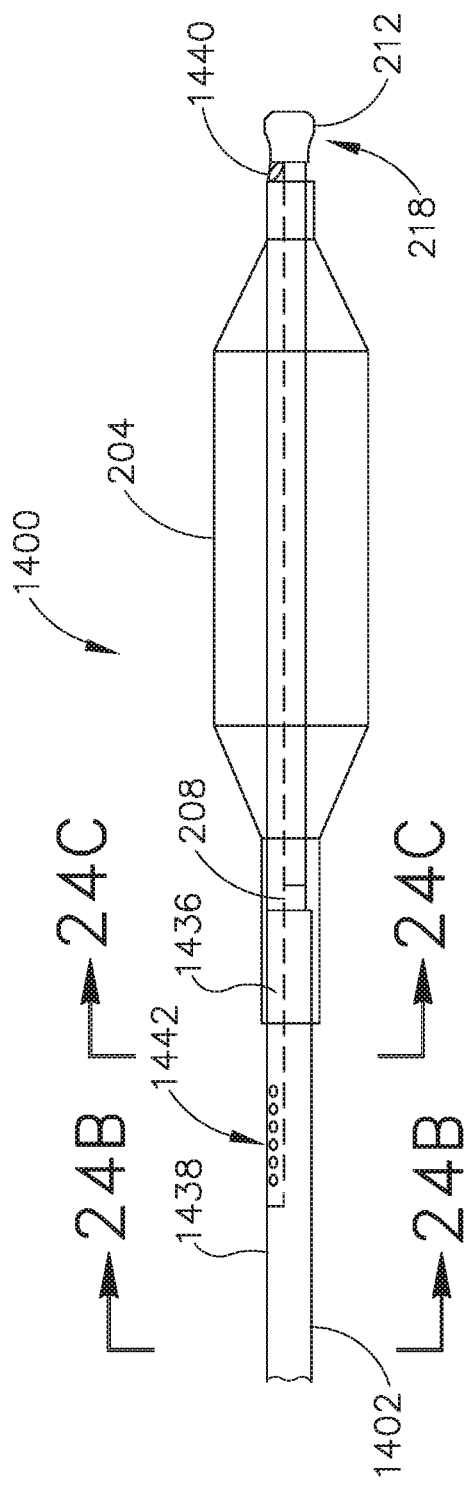
Fig.24A
Fig.24B
Fig.24C

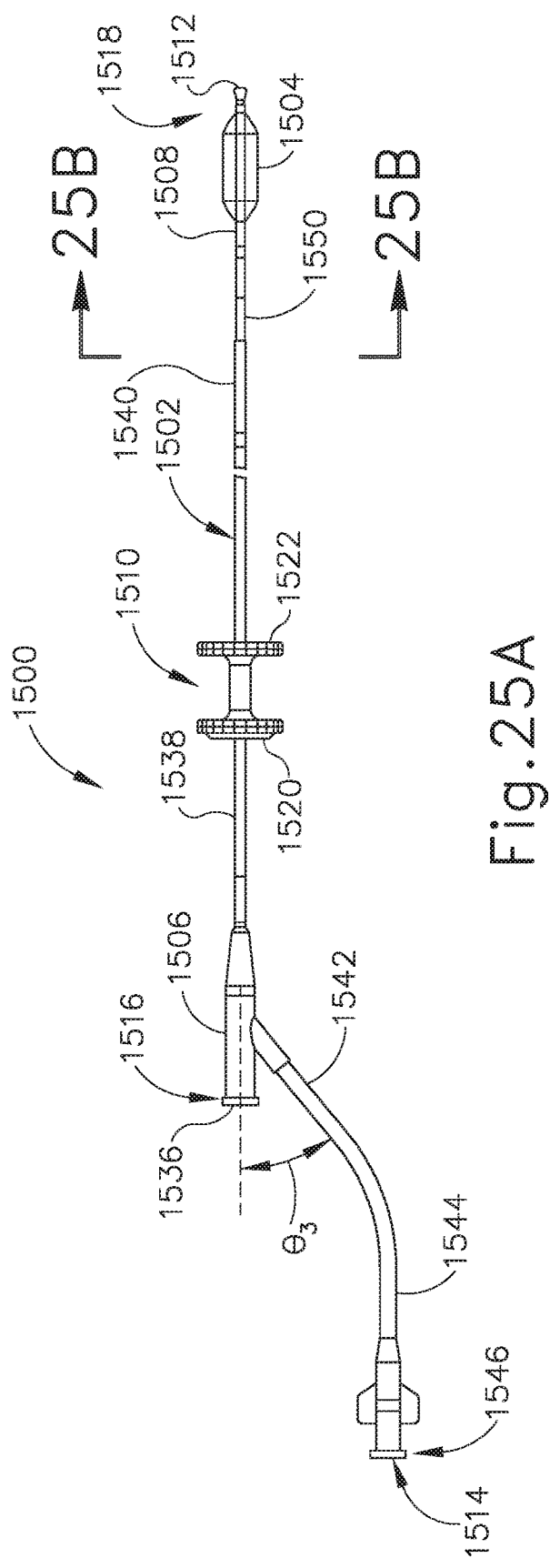
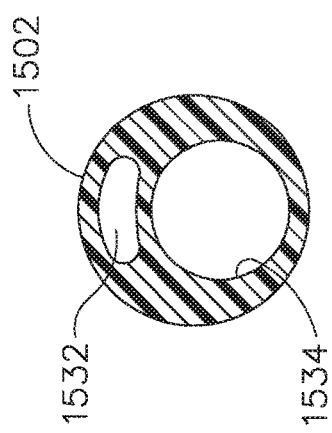
Fig.25A
Fig.25B

SYSTEM AND METHOD FOR ANESTHETIZING EUSTACHIAN TUBE This application is a continuation of U.S. patent application Ser. No. 14/928,423, filed Oct. 30, 2015, now U.S. Pat. No. 10,118,012, issued on Nov. 6, 2018.

BACKGROUND

Referring to FIGS. 1-2, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This occurs frequently in children in connection with an upper respiratory infection and accounts for the hearing impairment associated with this condition.

A lining membrane (mucous membrane) of the middle ear (14) and ET (26) is connected with, and is the same as, the membrane of the nose (42), sinuses (44) and throat (32). Infection of these areas results in mucous membrane swelling which in turn may result in obstruction of the ET (26). This is referred to as serous otitis media, which as discussed above is essentially a collection of fluid in the middle ear (14). Serous otitis media can be acute or chronic, and may be the result of blockage of the pharyngeal ostium (28) of the ET (26), which leads to the accumulation of fluid in the middle ear (14). In the presence of bacteria, this fluid may become infected, leading to an acute suppurative otitis media (infected or abscessed middle ear). When infection does not develop, the fluid remains until the ET (26) again begins to function normally, at which time the fluid is absorbed or drains down the tube into the throat (32) through the ET (26) pharyngeal ostium (28).

Chronic serous otitis media may result from longstanding ET blockage, or from thickening of the fluid so that it cannot be absorbed or drained down the ET (26). This chronic condition may lead to hearing impairment. There may be recurrent ear pain, especially when the individual catches a cold. Fortunately, serous otitis media may persist for many years without producing any permanent damage to the middle ear mechanism. The presence of fluid in the middle ear (14), however, makes it very susceptible to recurrent acute infections. These recurrent infections may result in middle ear damage.

When the ET (26) contains a build-up of fluid, a number of things may occur. First, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Treatment of this condition with antihistamines and decongestants can take many weeks to be fully effective. Finally, the fluid can become infected, which can lead to pain, illness, and temporary hearing loss. If the inner ear (14) is affected, the patient may feel a spinning or turning sensation (vertigo). The infection may be treated with antibiotics.

However, even if antihistamines, decongestants, and antibiotics are used to treat an infection or other cause of fluid build-up in the middle ear (14), these treatments may not immediately resolve the pain and discomfort caused by the buildup of fluid in the middle ear (14). The most immediate relief may be felt by the patient if the fluid can be removed from the ET (26).

Antibiotic treatment of middle ear infections may result in normal middle ear function within three to four weeks. During the healing period, the patient can experience varying degrees of ear pressure, popping, clicking and fluctuation of hearing, occasionally with shooting pain in the ear. Resolution of the infection may leave the patient with uninfected fluid in the middle ear (14), localized in the ET (26).

Fluid build-up caused by these types of infections may be treated surgically. The primary objective of surgical treatment of chronic serous otitis media may be to reestablish ventilation of the middle ear, keeping the hearing at a normal level and preventing recurrent infection that might damage the eardrum membrane and middle ear bones. One method to opening the ET (26) includes the "Valsalva" maneuver, accomplished by forcibly blowing air into the middle ear (14) while holding the nose, often called popping the ear. This method may be effective for opening the ET (26) but it may not clear the accumulated fluid from the middle ear (14) and is essentially a temporary fix when fluid is present in the middle ear (14).

Methods for treating the middle ear (14) and the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. patent application Ser. No. 14/317,269, entitled "Vent Cap for a Eustachian Tube Dilation System," filed Jun. 27, 2014, published as U.S. Patent Pub. No. 2015/0374963 on Dec. 31, 2015, issued as U.S. Pat. No. 10,350,396 on Jul. 16, 2019, the disclosure of which is incorporated by reference herein. As described in those references, functioning of the ET (26) may be improved by dilating the ET (26) with an expandable dilator instrument.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side elevational view of an exemplary guide catheter that may be used to position the dilation catheter of FIG. 5A.

FIG. 3B depicts a cross-sectional view of the guide catheter shown in FIG. 3A, taken along line 3B-3B of FIG. 3A.

FIG. 4 depicts an enlarged view of the distal end of the guide catheter shown in FIG. 3A.

FIG. 5A depicts a side elevational view of a balloon dilation catheter that may be used with the guide catheter of FIG. 3A.

FIG. 5B depicts a cross-sectional view of the balloon dilation catheter shown in FIG. 5A, taken along line 5B-5B of FIG. 6.

FIG. 6 depicts an enlarged view of the distal end of the balloon dilation catheter shown in FIG. 5A.

FIG. 8 depicts a perspective view of an exemplary endoscope suitable for use with the guide catheter of FIG. 3A and/or the balloon dilation catheter of FIG. 5A.

FIG. 9 depicts a side elevational view of the distal end of the endoscope of FIG. 8, showing an exemplary range of viewing angles.

FIG. 11 depicts a side elevational view of an exemplary needle that may be used with the guide catheter of FIG. 3A or the guide catheter FIG. 7 to deliver fluids to the Eustachian tube.

FIG. 12 depicts a side elevational view of an exemplary alternative needle that may be used with the guide catheter of FIG. 3A or the guide catheter FIG. 7 to deliver fluids to the Eustachian tube.

FIG. 18 depicts a side elevational view of another exemplary alternative needle that may be used to deliver fluids to the Eustachian tube.

FIG. 19 depicts an enlarged side view of the distal end of the needle of FIG. 18.

FIG. 20 depicts a cross-sectional view of the needle of FIG. 18, taken along line 20-20 of FIG. 19.

FIG. 21A depicts a side elevational view of an exemplary alternative balloon dilation catheter that may be used with the guide catheter of FIG. 3A or the guide catheter of FIG. 16.

FIG. 21B depicts a cross-sectional view of the balloon dilation catheter of FIG. 21A, taken along line 21B-21B of FIG. 22.

FIG. 22 depicts an enlarged side elevational view of the distal end of the balloon dilation catheter shown in FIG. 21A.

FIG. 23A depicts an enlarged side elevational view of an exemplary alternative balloon dilation catheter that may be used with the guide catheter of FIG. 3A or the guide catheter of FIG. 16.

FIG. 23B depicts a cross-sectional view of the balloon dilation catheter of FIG. 23A, taken along line 23B-23B of FIG. 23A.

FIG. 23C depicts a cross-sectional view of the balloon dilation catheter of FIG. 23A, taken along line 23C-23C of FIG. 23A.

FIG. 24A depicts an enlarged side elevational view of an exemplary alternative balloon dilation catheter that may be used with the guide catheter of FIG. 3A or the guide catheter of FIG. 16.

FIG. 24B depicts a cross-sectional view of the balloon dilation catheter of FIG. 24A, taken along line 24B-24B of FIG. 24A.

FIG. 24C depicts a cross-sectional view of the balloon dilation catheter of FIG. 24A, taken along line 24C-24C of FIG. 24A.

FIG. 25A depicts an enlarged side elevational view of an exemplary alternative balloon dilation catheter that may be used with the guide catheter of FIG. 3A or the guide catheter of FIG. 16.

FIG. 25B depicts a cross-sectional view of the balloon dilation catheter of FIG. 25A, taken along line 25B-25B of FIG. 25A.

DETAILED DESCRIPTION

Figure 1:
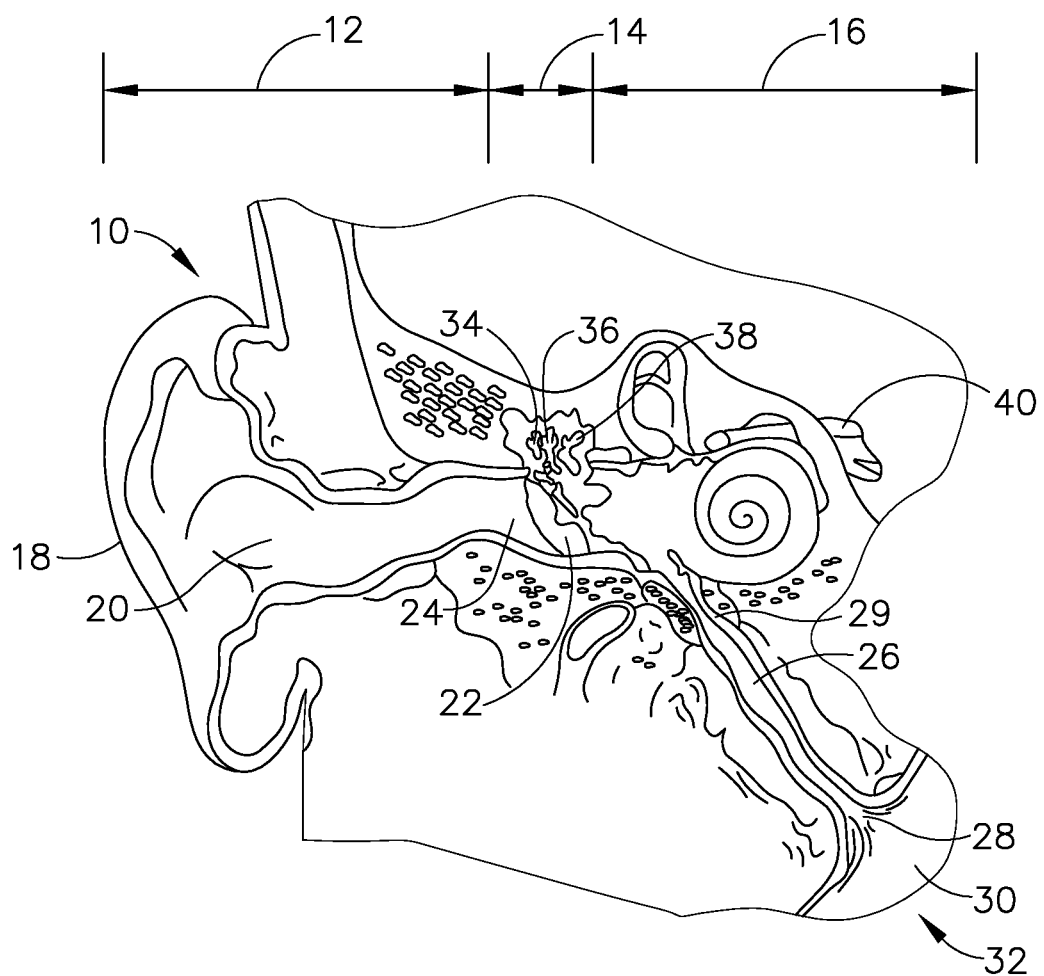
FIG. 1 depicts a cross-sectional view of a human ear showing the inner, middle and outer ear portions and the Eustachian tube connecting the middle ear with the nasopharynx region of the throat.
Figure 2:
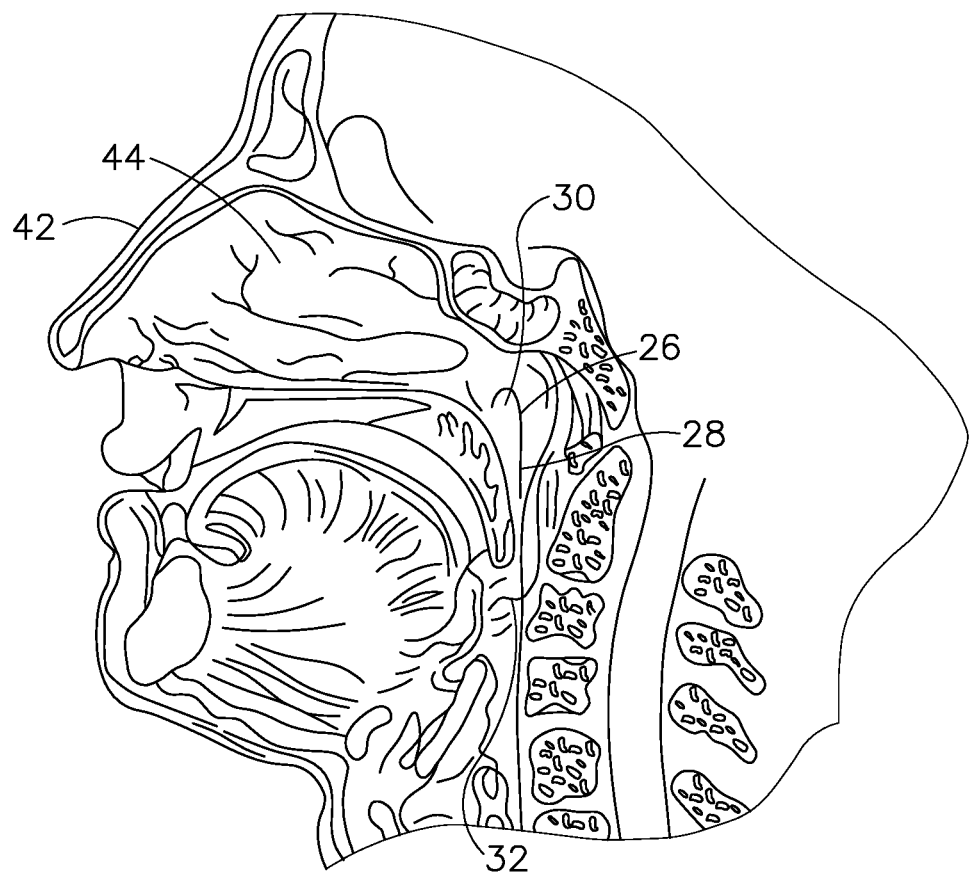
FIG. 2 depicts a cross-sectional view of a human head showing the nasopharynx region of the throat illustrated in FIG. 1 containing the pharyngeal ostium of the Eustachian tube illustrated in FIG. 1.

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. EXEMPLARY EUSTACHIAN TUBE DILATION CATHETER SYSTEM

One example of a treatment that may be performed to treat an ET (26) that does not provide sufficient communication between the middle ear (14) and the pharyngeal ostium (28) includes accessing and dilating the ET (26) using a guide catheter (100) and a balloon dilation catheter (200), examples of which are shown in FIGS. 3A-6. Guide catheter (100) of the present example includes an elongate tubular shaft (102) that has a proximal end (104), a distal end (106) and a lumen (108) therebetween. The guide catheter (100) may have any suitable length, diameter, angle of bend, and location of the bend along the length of the catheter (100), to facilitate accessing an ET (26) opening, such as the pharyngeal ostium (28). In some examples, the guide catheter (100) may have a length between about 8 cm and about 20 cm, or more particularly between about 10 cm and about 15 cm, or more particularly about 11 cm.

FIG. 3B is a cross-sectional view of the elongate tubular shaft (102) of guide catheter (100). As can be seen, shaft (102) has an outer shaft tube (110), an inner shaft tube (112) and a lumen (108). The outer shaft tube (110) may be constructed of a stiff material such as stainless steel and the inner shaft tube (112) may be constructed of a more flexible material such as a polymeric material including but not limited to nylon and further including a PTFE liner. The lumen (108) has a diameter of between about 2 mm and 3 mm, or more particularly between about 2.5 mm and about 2.6 mm, such that the balloon dilation catheter (200) can be easily inserted into the lumen (108) for dilation of the ET (26). The combination of guide catheter (100) and balloon catheter (200) may a compact system that is designed for a one-handed procedure. By "compact," it is intended that the length of the guide catheter shaft that is distal of the bend in the guide catheter is between about 0.5 and 2.0 about cm, in some versions between about 1 and about 2 cm, and in some versions about 1 cm. The compactness may help reduce interference with other instruments, such as an endoscope that may be used to help in visualizing the positioning of the system, as described below.

The distal portion (120) of guide catheter (100) is shown in an enlarged view in FIG. 4. The distal portion (120) of the guide catheter (100) may have a bend (122) with an angle between about 45 degrees and about 65 degrees, and more preferably between about 50 degrees and about 60 degrees, and particularly about 55 degrees, to facilitate access into the ET (26) via the pharyngeal ostium (28). The distal portion (120) of the guide catheter (100) is made of a transparent material such as a polymer including but not limited to nylon and PTFE such that balloon dilation catheter (200) is visible within the distal portion (120) and such that distal portion (120) is more flexible than the elongate shaft (102). The distal tip (124) of the distal portion (120) of the guide catheter (100) is made of PEBAX® (polyether block amide) such that it provides for atraumatic access to the ET (26), and may contain 20% barium sulfate or other similar radiopaque materials for visualizable access.

Referring again to FIG. 3A, the proximal portion (130) of guide catheter (100) includes a proximal hub (132) to aid in insertion of the balloon catheter into the ET (26). The hub (132) has a larger diameter proximal end (134) and a smaller diameter middle section (136) to facilitate stabilization of the guide catheter (100) in the nose, rotation of the guide catheter (100), and insertion of the balloon catheter (200) as will be described in further detail below. The hub (132) is ergonomically designed for insertion, location, and rotation through slight manipulations with one hand.

Balloon dilation catheter (200) of the present example is shown in FIG. 5A. The balloon dilation catheter (200) of the present example generally includes an elongate shaft (202) having a proximal end (214) and a distal end (218). The balloon dilation catheter (200) further includes a balloon (204) on the distal end (218) of the elongate shaft (202). The balloon (204) may be a polymer balloon (compliant, semi-compliant, or non-compliant). In some versions, the balloon (204) comprises a suitable non-compliant material such as but not limited to polyethylene terephthalate (PET), PEBAX® (polyether block amide), nylon or the like. The balloon catheter (200) may include any size of balloon including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm). The balloon dilation catheter (200) generally includes a proximally located connection (230) for inflating/activating the balloon (204) by communicating a pressurized medium (e.g., saline) to balloon (204).

Figure 10A:
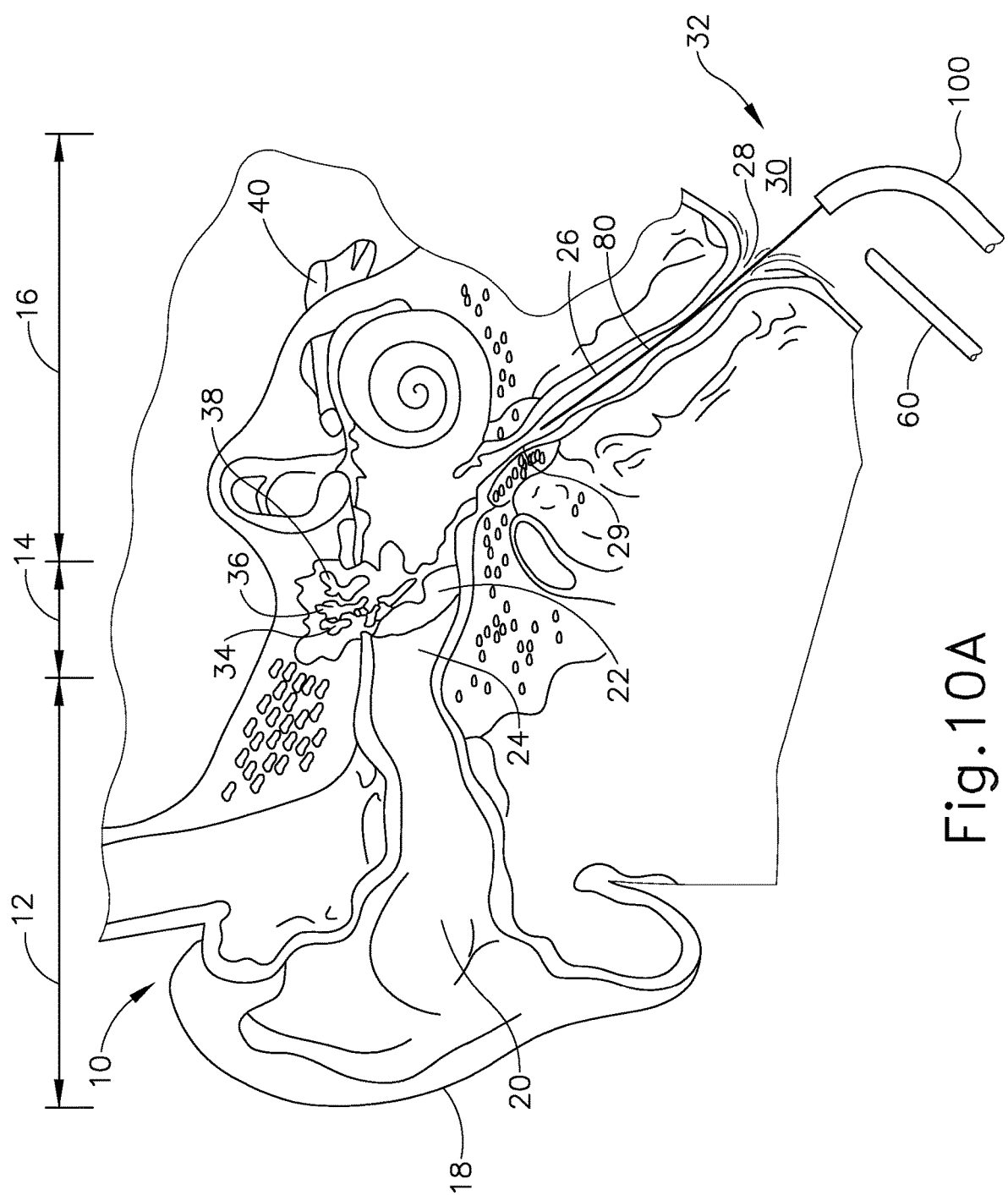
FIG. 10A depicts a cross-sectional view of a guide catheter, a balloon catheter, and an endoscope being positioned in relation to a Eustachian tube of a patient, with a guidewire disposed in the Eustachian tube.
Figure 10B:
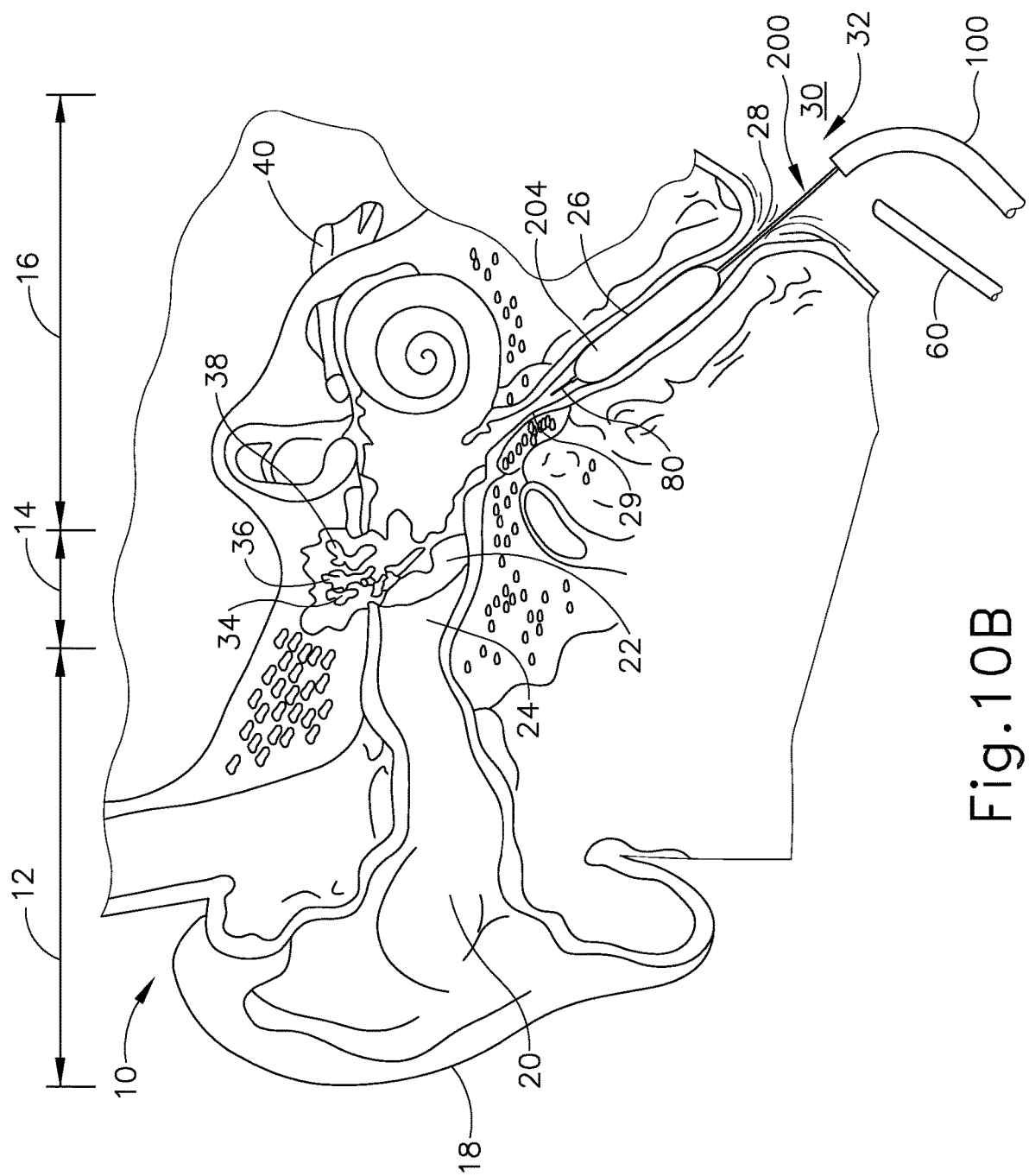
FIG. 10B depicts a cross-sectional view of the guide catheter, balloon catheter, and endoscope of FIG. 10A, with a balloon of the balloon catheter being expanded to dilate the Eustachian tube.
Figure 13:
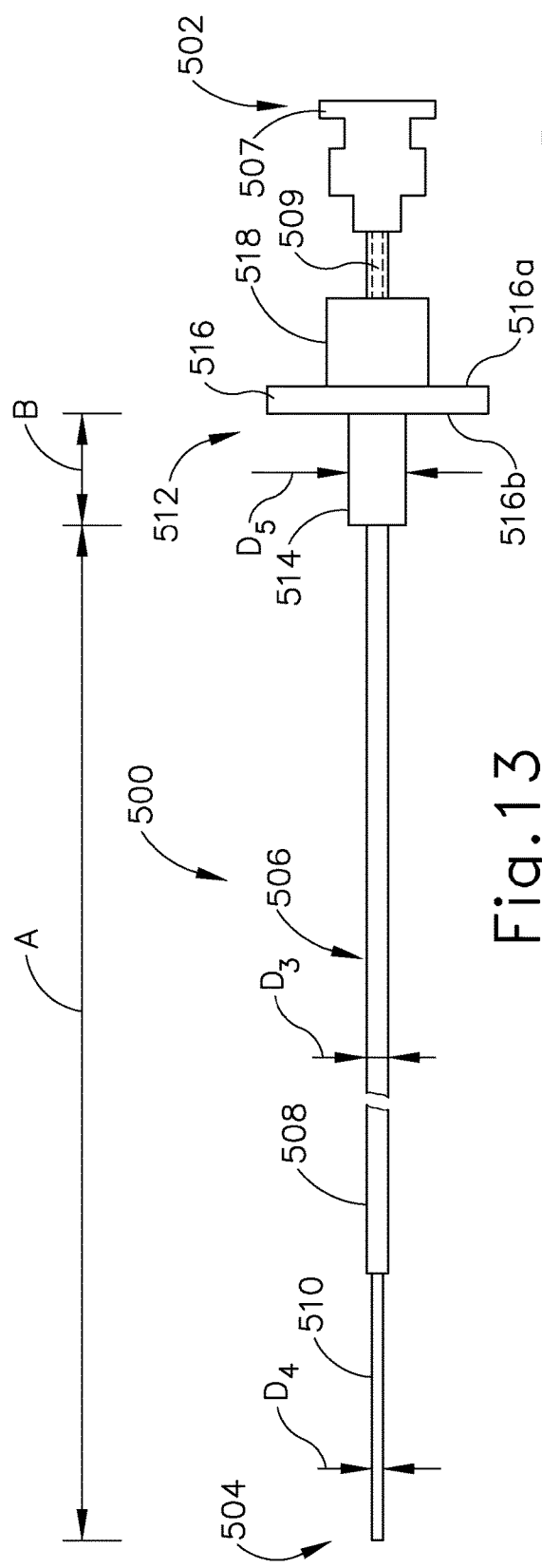
FIG. 13 depicts a side elevational view of another exemplary alternative needle that may be used with the guide catheter of FIG. 3A or the guide catheter FIG. 7 to deliver fluids to the Eustachian tube.

Balloon (204) may be expanded to dilate the ET (26) after balloon (204) is placed in a desirable location in the ET (26), as shown in FIGS. 10A-10B and described in greater detail below. For example, the opening area of the ET (26) includes a pharyngeal ostium (28), and dilation catheter (200) may be advanced to position the balloon in the pharyngeal ostium (28). An endoscope, such as endoscope (60) (FIGS. 8-9), may be used to assist in positioning the dilation catheter (200). Endoscope (60) may be advanced through the nasal passage to view the dilation catheter (200). A marker (208) on a shaft of the dilation catheter (200) can be viewed from endoscope (60) to approximate a location of the balloon (204) relative to the opening of the ET (26) (e.g., pharyngeal ostium (28)) based on a distance of the marker (208) from a proximal end of the balloon (204). Accordingly, dilation catheter (200) can be moved to place marker (208) in a desirable location before expansion of the balloon (204) in the ET (26).

Balloon dilation catheter (200) further includes an actuator (210). Actuator (210) has a proximal side 220 and a distal side (222). In the example shown in FIG. 5A, actuator (210) is secured by an adhesive to elongate shaft (202). The portion (240) of elongate shaft (202) that is distal of actuator (210) is sufficiently stiff to be guided through the nasal cavity and into the ET (26) and is constructed of stainless steel and preferably includes a stainless steel hypotube. The portion (238) of elongate shaft (202) that is proximal of actuator (210) and the portion (250) that is distal to portion (240) is more flexible than the portion (240) and is constructed of a polymeric material including but not limited to PEBAX® (polyether block amide). In this way, proximal portion (238) of elongate shaft (202) will not interfere with the endoscope (60) described above as it is advanced through the nasal passage, such that the dilation catheter (200) can be easily viewed. The actuator (210) allows for easy, ergonomic one-handed advancement of dilation catheter (200) through guide catheter (100) and into the ET (26). Actuator (210) may be used to advance or retract in alternative ways including but not limited to use of the thumb, the index finger, or a combination of fingers (e.g., the index and middle fingers) or the thumb and the index or middle finger.

The distal end (218) of balloon catheter (200) further includes a tip (212) and a flexible shaft portion (250) that is constructed of a polymeric material including but not limited to PEBAX® (polyether block amide) that extends from the distal end of the elongate shaft (202) to the proximal end of balloon (204). In the example shown in FIG. 5A, tip (212) is a bulbous polymeric blueberry shaped, atraumatic tip and is about 1.5 mm to about 2 mm in length, with an outer diameter of between about 2 mm and about 3 mm. The smoothness and roundness of tip (212) facilitates advancement of the balloon catheter (200) by helping it glide smoothly through the ET (26). Tip (212) further acts as a safety stop. The isthmus (29) of the ET (26), shown in FIG. 1 is approximately 1 mm in diameter. The tip (212) diameter is larger than the outer diameter (233) of the elongate shaft (202) shown in cross-section in FIG. 5B such that the tip (212) size will prevent the balloon catheter (200) from passing through the isthmus (29) into the middle ear (14).

After balloon (204) is positioned within the ET (26) and inflated to an expanded state (e.g., as shown in FIG. 10B), balloon (204) may be held in location while in an expanded state for an extended period of time (e.g. several seconds or minutes). The balloon catheter (200) may also deliver a substance to the ET (26), such as one or more of the therapeutic or diagnostic agents described herein. Balloon (204) may also carry an expandable stent for delivery into the ET (26) upon expansion of balloon (204). Balloon dilation catheter (200) and guide catheter (100) may be removed from the patient after balloon (204) has been deflated/unexpanded. The ET (26) will resume functioning, normally opening and closing to equalize atmospheric pressure in the middle ear (14) and protect the middle ear (14) from unwanted pressure fluctuations and loud sounds.

Figure 7:
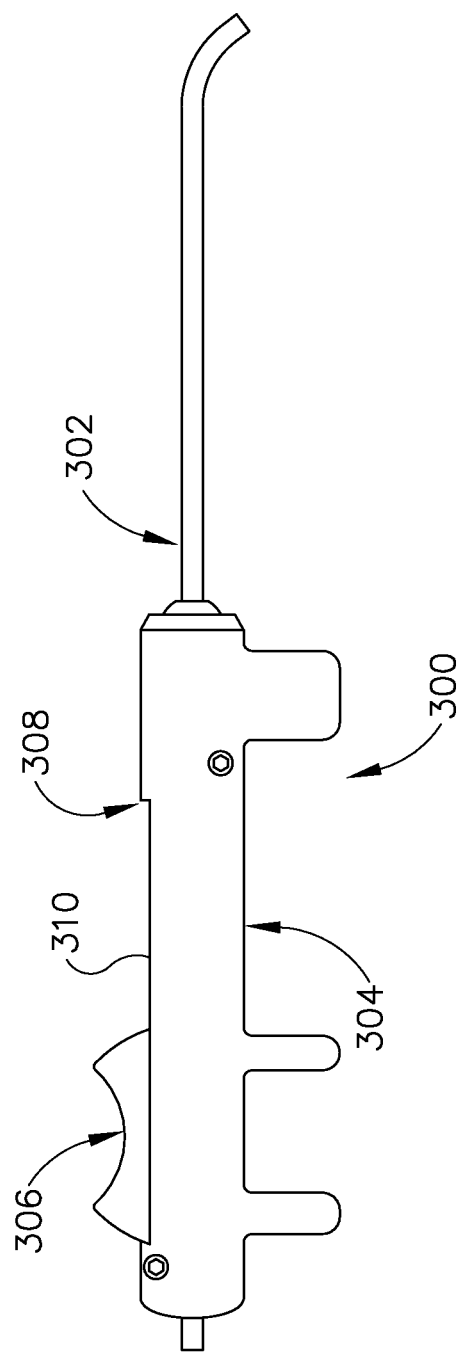
FIG. 7 depicts a side elevational view of another exemplary guide catheter that may be used to position the dilation catheter of FIG. 5A.

Another exemplary guide catheter (300) is shown in FIG. 7. In this example, proximal hub (132) is replaced with a handle (304). Guide catheter (300) comprises an elongate shaft (302) and a handle (304) to aid in insertion of a balloon catheter (200), such as balloon catheter (200), into the ET (26) in a manner similar to that described below with regard to the guide catheter (200). In the example shown in FIG. 7, an actuator (306) in the form of a slider is attached to portion of balloon catheter (200) that is contained within handle (304) and is slidably contained within elongate shaft (302) of guide catheter (300). Actuator (306) is thus slidable relative to handle (304) along a channel (310) to thereby selectively advance and retract balloon catheter (200) relative to elongate shaft (302). In use, elongate shaft (302) is inserted into the paranasal cavity of the patient and balloon catheter (200) is advanced into the ET (26) via thumb or single finger advancement of actuator (302) along channel (310) of handle (304). The advancement of balloon catheter (200) is continued until a visual marker indicates that advancement is complete, or until the enlarged tip (212) of balloon catheter (200) abuts the isthmus of the ET (26); or actuator (302) abuts the distal end (308) of channel (310) in handle (304) and is therefore fully deployed.

II. EXEMPLARY ENDOSCOPE

Referring to FIGS. 8-9, an endoscope (60) may be used to provide visualization within an anatomical passageway (e.g., within the oro-nasal cavity, etc.) during the process using guide catheter (100) and/or balloon catheter (200) just described, for example. Endoscope 60 of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

As noted above, an endoscope (60) may be used to provide visualization within an anatomical passageway (e.g., within the nasal cavity, etc.) during a process of using dilation catheter system, which in one example includes the balloon dilation catheter (200, 300) and, optionally, guide catheter (100). As shown in FIGS. 8-9, endoscope (60) of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. EXEMPLARY METHOD OF TREATING THE EUSTACHIAN TUBE

FIGS. 10A-10B show schematic versions of the guide catheter (100) and balloon catheter (200) being used to treat the ET (26) under visual guidance using endoscope (60). In use, guide catheter (100) may be advanced into a nostril and through a nasal cavity to position a distal end of the catheter (100) at, in or near the pharyngeal ostium (28), which opens into the ET (26). In some instances, the guide catheter (100) may be passed through a nostril to the ET (26) on the ipsilateral (same side) of the head. In some other instances, the guide catheter (100) may be passed through a nostril to the ET (26) on the contralateral (opposite side) of the head. A guiding element such as a guidewire (80) or illuminating fiber may be used to aid in accessing the ET (26). In some versions, guidewire (80) is omitted.

As shown in FIG. 10B, after guide catheter (100) is in a desired position, balloon catheter (200) is advanced through the guide catheter (100) to position balloon (204) of balloon catheter (200) within the ET (26). The physician/user may place the index and middle fingers on either side of the smaller diameter middle section (136) of proximal hub (132) of guide catheter (100). The physician/user will then place the thumb on the proximal side (220) of actuator (210) or within both sides of the actuator (210) and will use the thumb to slide the balloon dilation catheter (200) through guide catheter (100) to position balloon (204) within the ET (26). Alternatively, the user may grasp proximal hub (132) of guide catheter (100) and use the index finger placed on the proximal side (220) of actuator (210) or in between the distal side (222) and the proximal side (220) of actuator (210) to advance balloon catheter (200). The larger diameter tip (212) prevents balloon catheter (200) from advancing past the isthmus (29) and into the middle ear (14). Further, distal side (222) of actuator (210) will bottom out against proximal end (104) of guide catheter (100), such that the balloon catheter (200) cannot advance any further. The actuator (210) thus prevents the balloon catheter (200) from reaching passing the isthmus (29) and reaching the middle ear (14). Further, actuator (210) can be positioned at the appropriate distance along the elongate shaft (202) such that access to the ET (26) may be from the contralateral or the ipsilateral side.

In an alternative example, a balloon catheter (200) is advanced into a nostril of a patient without the use of a guide catheter (100). The balloon (204) of the balloon catheter (200) is placed within the ET (26). The physician/user will advance the balloon catheter (200) until the proximal side (220) of the actuator (210) is adjacent the patient's nostril. The distal side (222) of the actuator (210) will bottom out against the patient's nostril, such that the balloon catheter cannot advance any further. The actuator (210) prevents the catheter from passing the isthmus (29) and reaching the middle ear (14). Further, actuator (210) can be positioned at the appropriate distance along the elongate shaft (202) such that access to the ET (26) may be from the contralateral or the ipsilateral side.

Any number of procedures may be carried out following placement of the balloon catheter (200) into the desired position as described above. For instance, the Eustachian tube (ET) may be dilated by communicating fluid to balloon (204) and thereby inflating balloon (204), in accordance with the teachings of various reference cited herein or otherwise. In addition or in the alternative, the isthmus (29) may be cleaned and/or otherwise treated as described in U.S. Patent Application No. 62/139,919, entitled "Method and Apparatus for Cleaning Isthmus of Eustachian Tube," filed Mar. 30, 2015, the disclosure of which is incorporated by reference herein.

The elongate shaft (202) contains adjacent dual lumen (232, 234) tubing (see FIG. 5B). By adjacent dual lumen tubing, it is intended that the lumens (232, 234) are next to each other but are spaced apart, one from the other. The inflation lumen (232) is used for inflation of the balloon (204) with water, contrast medium, or saline through inflation port (230) to a pressure of between about 3 and about 15 atmospheres, or of between about 6 and about 12 atmospheres. The injection lumen (234) permits the optional injection of water, medicament, or even the introduction of a guidewire (80) through the injection port (236) at the proximal end (216) of the proximal connector (206). In order to ensure that inflation port (230) is used for balloon (204) inflation only, inflation port (230) and injection port (236) may optionally have different type connectors. For example, inflation port (230) may be a female connector whereas injection port (236) is a male connector or vice versa. Alternatively, injection port (236) may have a right-handed thread connector and inflation port (230) may have a left-handed thread connector or vice versa.

It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used in this invention include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813 (Lin et al.,) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112," manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular example, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered in this invention may include various antihistamines such as azelastine (e.g., Astylin) diphenhydramine, loratidine, etc.

Additionally or alternatively, in some examples such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, *bacillus* calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In one example, a local anesthetic, such as Lidocaine is injected through the injection lumen (234) prior to dilation of the ET (26). The injection lumen (234) can be used for venting during dilation so that pressure in the middle ear (14) does not increase or decrease.

IV. EXEMPLARY SYSTEMS FOR DELIVERING ANESTHESIA TO THE EUSTACHIAN TUBE

Use of local anesthesia may improve patient pain management in treatments of the ET (26). Due to the anatomical size constraints of the ET (26) and other structures, practitioners must utilize small-size needles to access the ET (26) and adjacent structures. However, existing off-the-shelf, small-size needles may lack stiffness, pushability, and other advantageous properties that allow a practitioner to readily access and anesthetize the ET (26). Therefore, certain ET (26) treatments and procedures that may otherwise be performed in a less costly outpatient (i.e., in-office) setting may end up being performed in a hospital setting under general anesthesia. Improving the current needles and systems for delivering anesthesia to the ET (26) may therefore provide access to a wider population of patients needing ET (26) treatments and increase the comfort of patients receiving in-office ET (26) treatments. The following examples provide various devices and techniques that may be used to readily deliver anesthetic and/or other kinds of fluid to an ET (26) without requiring hospitalization of the patient. Several examples of the various kinds of fluids that may be delivered using the below-described devices and techniques are referred to above. Other examples of fluids that may be delivered using the below-described devices and techniques will be apparent to those of ordinary skill in the art in view of the teachings herein.

A. Exemplary Needle Including Reduced Diameter Distal Portion

FIG. 11 shows an exemplary alternative needle (400) that may be used to access and anesthetize the ET (26). Needle (400) may be fluidly coupled with a source of fluid in a syringe, for example, and directed into the ET (26) with or without a guide catheter (100, 300), to deliver an anesthetic fluid to the ET (26). It will be understood that in addition or in the alternative, needle (400) may be utilized to deliver a non-anesthetic, therapeutic fluid and/or any other suitable kinds of fluids to the ET (26). As shown, needle (400) includes a proximal end (402), an open distal end (404), and a shaft (406) extending therebetween. Needle (400) defines a lumen (409) that extends continuously through the length of shaft (406). Proximal end (402) includes a female luer component (407) that is configured to be mechanically and fluidly coupled with a source of fluid, such as a syringe, tubing, etc, such that fluid may be communicated through lumen (409) and out of distal end (404).

In the present example, a first, more proximal portion (408) of shaft (406) includes a first cross-sectional dimension ($D_1$), and a second, more distal portion (410) of shaft (406) includes a second cross-sectional dimension ($D_2$), providing a neck-down at distal portion (410). The first cross-sectional dimension ($D_1$) is larger than the second cross-sectional dimension ($D_2$), such that proximal portion (408) is relatively stiffer to provide pushability; while distal portion (410) provides flexibility, which may prevent damage to an anatomical structure as needle (400) is advanced therethrough. Needle (400) includes sufficient flexibility in order to traverse the bend (122) of guide catheter (100) (or bends in the anatomy), for example, but also includes sufficient stiffness to provide pushability through guide catheter (100) and/or the ET (26). In the example shown, shaft (406) and luer component (407) are made from Type 304 Stainless Steel. However, shaft (406) and luer component (407) may instead be made from any other suitable material(s) as will be understood by persons skilled in the art in view of the teachings herein.

In the present example, the first cross-sectional dimension (D1) is about 0.050 inches, and the second cross-sectional dimension (D2) is about 0.0165 inches. In other examples, the first cross-sectional dimension (D1) may be between about 0.030 inches and about 0.060 inches, while the second cross-sectional dimension (D2) may be between about 0.015 inches and about 0.040 inches. In the present example, needle (400) is cylindrical in shape and therefore the first and second cross-sectional dimensions (D1, D2) are outer diameters of the respective portions (408, 410) of needle (400). In the present example, the inner diameter (i.e., of lumen (409)) at the first portion (408) is about 0.028 inches, while the inner diameter at the second portion (410) is about 0.008 inches. In other examples, the inner diameter at first portion (408) may be between about 0.018 inches and about 0.040 inches, while the inner diameter of second portion (410) may be between about 0.008 inches and about 0.010 inches. It will be understood that where needle (400) includes a cross-sectional shape other than a circle, first and second cross-sectional dimensions (D1, D2) and inner cross sectional dimensions (i.e., of lumen (409)) may have other characteristics.

In the present example, needle (400) does not include a taper between the proximal and distal portions (408, 410) and instead includes a stepped transition between proximal and distal portions (408, 410). In some other versions, needle (400) may include a tapered transition between proximal and distal portions (408, 410). Shaft (406) of the present example includes a length of about 8 inches, but in other examples length of shaft (406) may be between about 6 inches and about 10 inches. In the present example, proximal portion (408) includes a length of about 7 inches and distal portion includes a length of about 1 inch. Alternatively, proximal portion (408) and distal portion (410) may have any other suitable lengths. For example, proximal portion (408) may include a length of between about 5 inches and about 9 inches, while distal portion may include a length of between about 0.5 inches and about 2.5 inches.

In some examples, it may be advantageous to provide a preformed bend in the needle to access the ET (26). FIG. 12 shows an exemplary alternative needle (420) that is substantially identical to needle (400), except for that distal end (424) of needle (420) includes a bend (426) in shaft (426), such that a distal portion of needle (420) is disposed at an oblique angle (θ1) relative to the longitudinal axis (427). In the present example, angle (θ1) is about 20 degrees, but in other examples may be between about 5 degrees and about 30 degrees. As shown, a reduced cross-sectional distal portion (430) and part of the larger cross-sectional dimension proximal portion (428) is disposed at angle (θ1) relative to axis (427). In the present example, proximal and distal portions (428, 430) have the cross-sectional dimensions (D1, D2) described above. Moreover, other dimensions of shaft (426) and proximal and distal portions (428, 430) are the same or similar to those disclosed with respect shaft (406) and proximal and distal portions (408, 410), respectively.

B. Exemplary Alternative Needle and Sheath including Predetermined Spatial Relationship FIGS. 13-15B show an exemplary alternative needle (500) and sheath (600) that may be utilized with guide catheter (100), as shown in FIG. 15, or guide catheter (300), in order to access and deliver therapeutic fluids to the ET (26). As discussed in further detail below, in the present example, needle (500) and sheath (600) include features that allow sheath (600) to be fixed relative to guide catheter (100) and that prevent the tip of needle (500) from protruding beyond a predetermined distance past the distal end of guide catheter (100).

Needle (500) may be fluidly coupled with a source of fluid in a syringe, for example, and directed into the ET (26) under the guidance of sheath (600) and guide catheter (100) to deliver an anesthetic fluid to the ET (26). It will be understood that in addition or in the alternative, needle (500) may be utilized to deliver a non-anesthetic, therapeutic fluid and/or any other suitable kinds of fluids to the ET (26). As shown, needle (500) includes a proximal end (502), a distal end (504), and a shaft (506) extending therebetween. Needle (500) further defines a lumen (509) that extends continuously along the length of shaft (506). Proximal end (502) includes a female luer component (507) that is configured to be mechanically and fluidly coupled with a source of fluid, such as a syringe, tubing, etc, such that fluid may be communicated through lumen (509) and out of distal end (504).

In the present example, a first, more proximal portion (508) of shaft (506) includes a first cross-sectional dimension ($D_3$), and a second, more distal portion (510) of shaft (506) includes a second cross-sectional dimension ($D_4$), providing a neck-down at distal portion (510). The first cross-sectional dimension ($D_3$) is larger than the second cross-sectional dimension ($D_4$), such that proximal portion (508) is relatively stiffer to provide pushability; while the distal portion (510) provides additional flexibility, which may prevent damage to an anatomical structure as needle (500) is advanced therethrough. Needle (500) includes sufficient flexibility in order to traverse the bend (122) of guide catheter (100) (or bends in the anatomy), for example, but also includes sufficient stiffness to provide pushability through guide catheter (100) and/or the ET (26). In the example shown, shaft (506) and luer component (507) are made from Type 304 Stainless Steel. However, shaft (506) and luer component (507) may instead be made from any other suitable material(s) as will be understood by persons skilled in the art in view of the teachings herein.

In the present example, first cross-sectional dimension ($D_3$) is 0.034 inches, but in other examples it may be between about 0.03 inches and about 0.06 inches. Second cross-sectional dimension ($D_4$) is 0.0165 inches, but in other examples it may be between about 0.015 inches and about 0.040 inches. In the present example, the inner diameter (i.e., of lumen (509)) at the first portion (508) is about 0.025 inches, while the inner diameter at the second portion (510) is about 0.008 inches. In other examples, the inner diameter at first portion (508) may be between about 0.018 inches and about 0.040 inches, while the inner diameter of second portion (410) may be between about 0.008 inches and about 0.010 inches.

As shown, needle (500) includes a stop member (512) that is coupled to shaft (506) and is configured to limit a distal advancement of needle (506) relative to sheath (600) and balloon catheter (200), as discussed in further detail below.

In the present example, stop member (512) is fixedly coupled to shaft (506) and includes an elongate first portion (514) having a cross-sectional dimension ($D_5$) and a length (B); and a second portion in the form of a circular stop flange (516) positioned proximal to the first portion (514). As shown, flange (516) includes a proximal side (516a) and distal side (516b). A third portion (518) extends proximally from flange (516). As shown, shaft (506) extends distally from first portion (514) includes a length (A). In the present example, the length (A) is approximately 19 cm. Alternatively, any other suitable length may be used.

Figure 14:
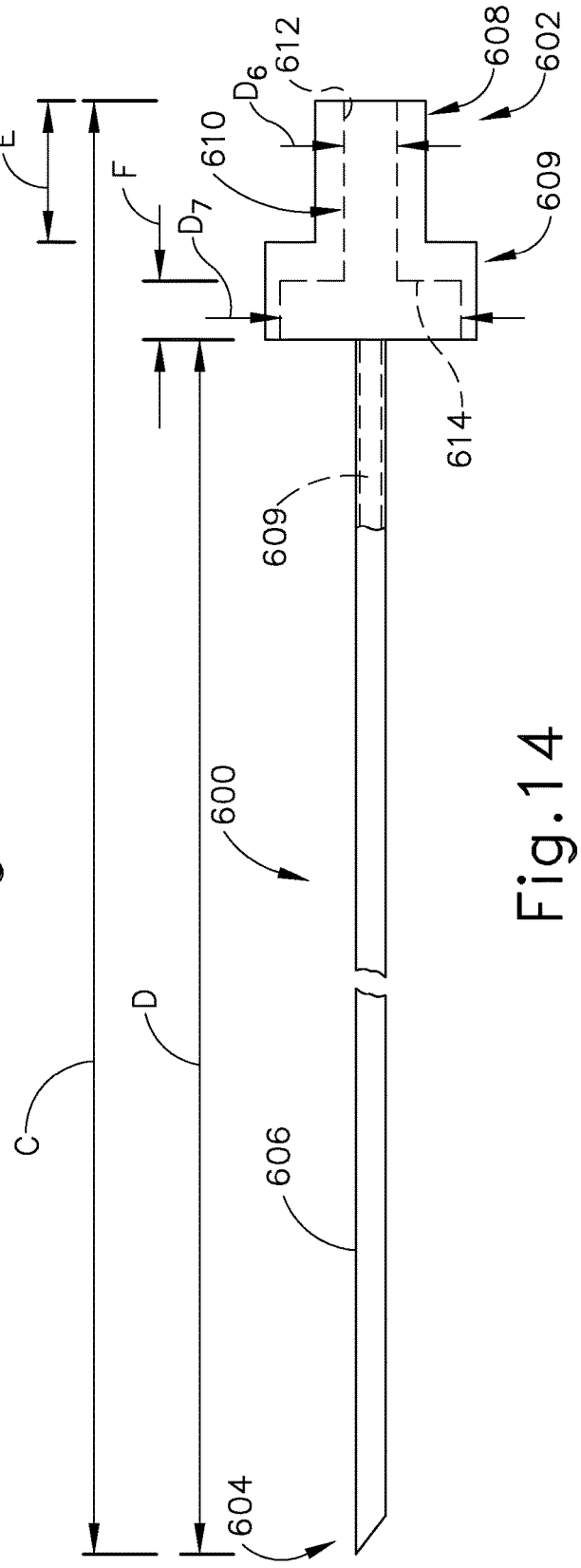
FIG. 14 depicts a side elevational view of an exemplary sheath that may be used with the needle of FIG. 13 and the guide catheter of FIG. 3A or the guide catheter FIG. 7 to deliver fluids to the Eustachian tube.

As shown in FIG. 14, sheath (600) includes a proximal end (602), a distal end (604), and a shaft (606) extending therebetween. Sheath (600) defines a lumen (609) extending continuously along the length of shaft (606). Proximal end (602) includes a stop hub (608). Stop hub (608) includes an opening (610) extending continuously through hub (608) and in communication with lumen (609). Opening (610) includes a first portion (612) with a cross-sectional dimension ($D_6$) and length (E); and a second portion (614) with a cross-sectional dimension ($D_7$) and length (F). Sheath (600) includes an overall length (C), with shaft (606) including a length of (D) and hub (608) including a length E+F (dimensions E and F are discussed in more detail below). In the present example, length C is about 8 inches, but in other examples, it may be between about 6 inches and about 10 inches, while length D is about 9 inches, but in other examples, it may be between about 7 inches and 10 inches. As shown, cross-sectional dimension (D7) is greater than cross-sectional dimension (D6). In the present example, cross-sectional dimension (D6) is about 0.05 inches, but in other examples, it may be between about 0.03 inches and about 0.06 inches.

Figure 15A:
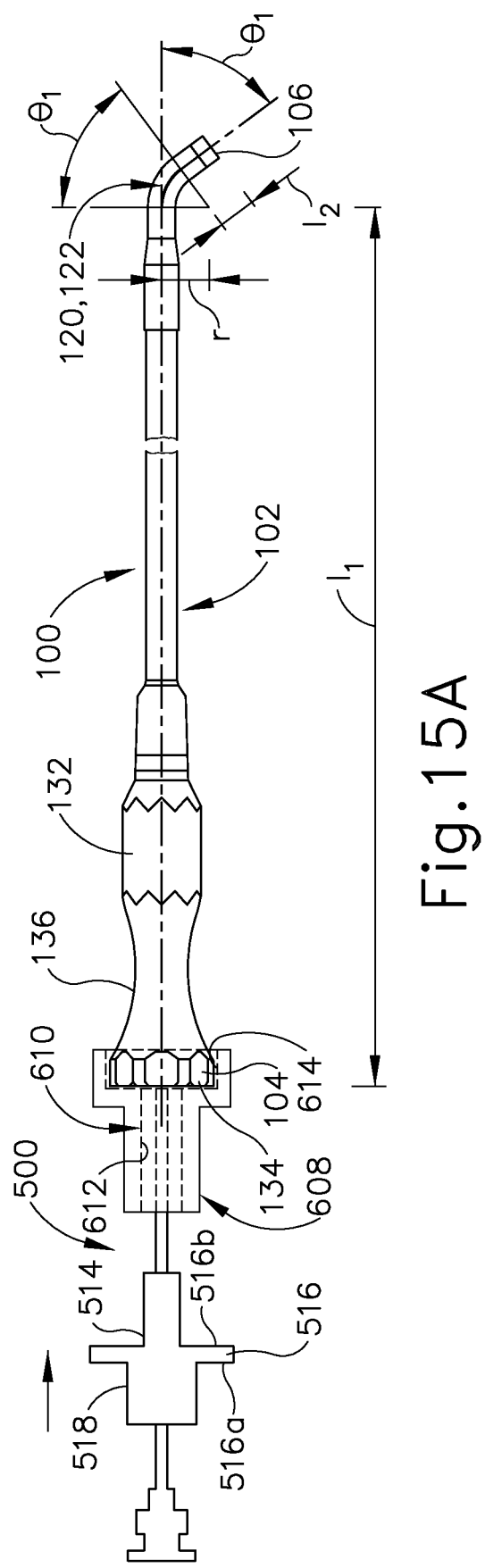
FIG. 15A depicts a side elevational view of the needle of FIG. 13 and the sheath of FIG. 14 having been directed into the guide catheter of FIG. 3A, with a hub of the sheath abutted against a handle portion of the guide catheter, and the needle being in a proximal, retracted position.
Figure 15B:
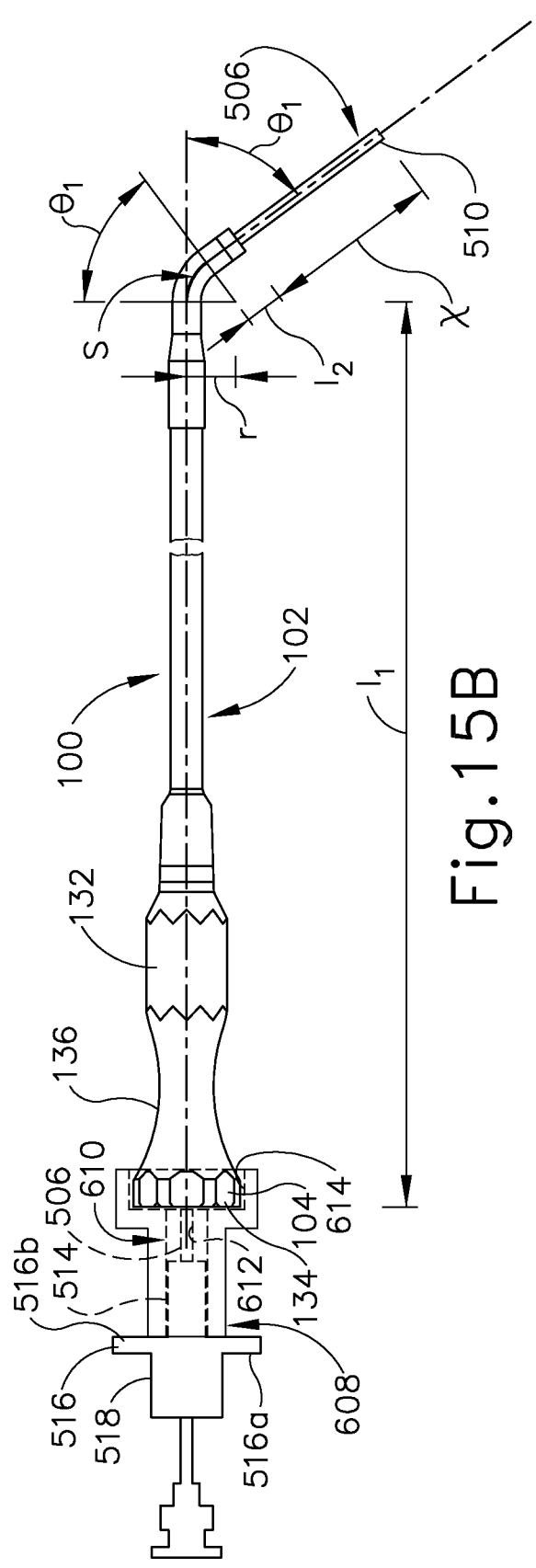
FIG. 15B depicts a side elevational view of the needle of FIG. 13 and the sheath of FIG. 14 having been directed into the guide catheter of FIG. 3A, with the hub of the sheath abutted against a handle portion of the guide catheter and the needle being in a distal, exposed position.

As shown in FIGS. 15A-15B, needle (500) may be directed into lumen (609) of sheath (600), which may be directed into lumen (108) of balloon catheter (100), in any sequence. As shown, first portion (612) of opening (610) is configured to receive first portion (514) of stop member (512). Therefore, in the present example, cross-sectional dimension ($D_5$) is less than cross sectional dimension ($D_6$). Second portion (614) of opening (610) is configured to lockingly receive proximal end (134) of guide catheter (100). In the present example, second portion (614) (i.e., cross-sectional dimension (D7)) is sized such that proximal end (134) of guide catheter (100) is coupled to second portion (614) in an interference fit manner. In other examples, second portion (614) and proximal end (134) may be removably coupled to one another by other suitable features, such as complementary threads, snap fitting, resilient features, etc.

In some examples, needle (500) is directed into sheath (600) prior to the needle (500) and sheath (600) being directed into guide catheter (100), such that needle (500) and sheath (600) are directed into guide catheter (100) as a unit. In some other examples, sheath (600) may be directed into guide catheter (100) prior to needle (500) being inserted into sheath (600). In any of these examples, guide catheter (100) may be directed into the oro-nasal cavity with the sheath (600) and needle (500) as a unit; guide catheter (100) may be directed into the oro-nasal cavity alone (i.e., before sheath (600) and needle (500) are disposed in guide catheter (100)).

In the present example, guide catheter (100), needle (500), and sheath (600) are directed into the oro-nasal cavity as a unit, in the manner shown in FIG. 15A, such that no portion of shaft (506) of needle (500) protrudes from distal end (106) of guide catheter (100). Once the guide catheter (100) is properly placed relative to the ET (26), for example, an operator may advance needle (500) distally relative to sheath (600) and catheter (100) such that distal side (516b) of flange (516) abuts stop hub (608). In the example shown, needle (500), sheath (600), and guide catheter (100) are sized and configured such that when proximal end (134) of guide catheter (100) is removably coupled to second portion (614) of sheath (600), and when flange (516) abuts stop hub (608), shaft (506) of needle (500) protrudes from distal end (106) of guide catheter (100) a predetermined distance x. Then, an operator may direct fluid through lumen (509) and out of distal end of shaft (506) into the ET (26), for example. In the present example, distance x is 10 mm, but in other examples x may be between about 5 mm and about 25 mm.

In the example shown, x=A+B+E−F−l, where l is the overall length of guide catheter (100). As shown in FIGS. 15A-15B, $l=l_1+l_2+s$, where $l_1$ equals the length of the portion of guide catheter (100) proximal to bend (120), $l_2$ equals the length of the portion of guide catheter (100) distal to bend (120), and s equals the length of curved portion at bend (120) of guide catheter (100). It will be understood that $s=2\pi r\theta_1/360$, with r shown in FIGS. 15A-15B. In the present example, l is approximately 15.5 cm, but in other examples may be between about 12 cm and about 18 cm. As shown, $l_1$ is about 14 cm, but in other examples may be between about 13 cm and about 17 cm, while $l_2$ is about 1.5 cm, but in other examples may be between about 1 cm and about 3 cm. As shown, s is about 0.5 cm, but in other examples, s may be between about 0.2 cm and about 1 cm. Further, as will be understood by person skilled in the art, s depends on angle ($\theta_1$) and radius r. In the present example, $\theta_1$ is between about 45 degrees and about 65 degrees, and more preferably between about 50 degrees and about 60 degrees, and particularly about 55 degrees, to facilitate access into the ET (26) via the pharyngeal ostium (28). However, in other examples, $\theta_1$ may be between about 30 degrees and about 70 degrees.

In the example shown, A+B is the overall length of the portion of needle (600) distal to stop flange (516), E is the length/depth of second portion (614) into which proximal end (134) of guide catheter (100) is lockingly received, and F is the distance between proximal end of stop member (608) and the proximal end of second portion (614) (and thus also the distance between second side (516b) of stop flange (516) and proximal end (134) of guide catheter (100) when stop flange (516) abuts stop hub (608) and proximal end (134) of guide catheter (100) is received in second portion (614) (FIG. 15B)). As shown, A is about 8 inches, but in other examples may be between about 6 inches and about 10 inches, while B is about 1 inch, but in other examples may be between about 0.5 inches and about 2.5 inches. As shown, E is about 2 inches, but in other examples, s may be between about 1 inch and about 3 inches. In the present example, F is about 0.25 inches, but in other examples may be between about 0.25 inches and about 0.5 inches.

C. Exemplary Alternative Guide Catheter and Modified Needle

Figure 16:
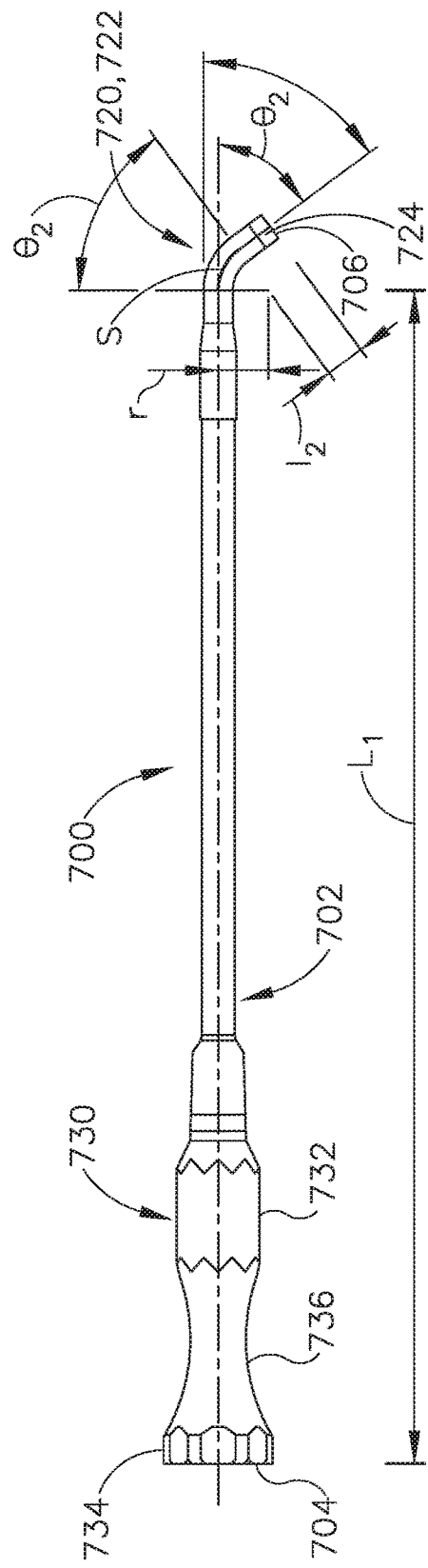
FIG. 16 depicts a side elevational view of an exemplary alternative guide catheter.

FIG. 16 shows an exemplary alternative guide catheter (700). Guide catheter (700) of the present example includes an elongate tubular shaft (702) that has a proximal end (704), a distal end (706) and a lumen (708) therebetween. The guide catheter (700) may have any suitable length, diameter, angle of bend, and location of the bend along the length of the catheter (700), to facilitate accessing an ET (26) opening, such as the pharyngeal ostium (28). In the present example, the guide catheter (700) has a length L, discussed in further detail below. In the example shown, L may be between about 8 cm and about 20 cm, or more particularly between about 10 cm and about 15 cm, or more particularly about 11 cm.

In the present example, shaft (702) is constructed of type 304 stainless steel. In addition or in the alternative, shaft (702) may include an inner shaft tube (not shown) constructed of a more flexible material such as a polymeric material including but not limited to nylon and further including a PTFE liner. It should also be understood that a proximal portion of shaft (702) may be constructed of a rigid material (e.g., steel) while a distal portion of shaft (702) is constructed of a more flexible material (e.g., polymer). The lumen (708) may have a diameter of between about 2 mm and 3 mm, more particularly between about 2.5 mm and about 2.6 mm, such that the balloon dilation catheter (200) can be easily inserted into the lumen (708) for dilation of the ET (26).

The combination of guide catheter (700) and balloon catheter (200) may provide a compact system that is designed for a one-handed procedure. By "compact," it is intended that the length of shaft (702) that is distal of the bend (722) in shaft (702) is between about 0.5 cm and about 2.0 cm, in some versions between about 0.7 cm and about 1.7 cm, and in some versions about 1.0 cm. The compactness may help reduce interference with other instruments, such as an endoscope that may be used to help in visualizing the positioning of the system, as described above.

The distal portion (720) of the guide catheter (700) may have a bend (722) with an angle between about 45 degrees and about 65 degrees, and more particularly between about 50 degrees and about 60 degrees, and most particularly about 55 degrees, to facilitate access into the ET (26) via the pharyngeal ostium (28). In the present example, distal portion (720) of guide catheter (700) is made of a transparent material such as a polymer including but not limited to nylon and PTFE such that balloon dilation catheter (200) is visible within distal portion (720) and such that distal portion (720) is more flexible than the remainder of elongate shaft (702). In the present example, distal tip (724) of distal portion (720) of guide catheter (700) is made of Type 304 stainless steel, and may contain 20% barium sulfate or other similar radiopaque materials for visualizable access. Of course, any other suitable material(s) may be used.

In the present example, length L of guide catheter (720) equals L1+L2+S, where L1 is the distance between proximal end (734) and proximal end of bend (722), L2 is the distance between distal end of bend (722) and distal end (706) and S is the length of curved portion of bend (722). In the present example, $S=2\pi r\theta_2/360$, with r shown in FIG. 16.

Proximal portion (730) of guide catheter (700) includes a proximal hub (732) to aid in insertion of the balloon catheter into the ET (26). The hub (732) has a larger diameter proximal end (734) and a smaller diameter middle section (736) to facilitate stabilization of the guide catheter (700) in the nose, rotation of the guide catheter (700), and insertion of the balloon catheter (200) as will be described in further detail below. The hub (732) is ergonomically designed for insertion, location, and rotation through slight manipulations with one hand.

Figure 17:
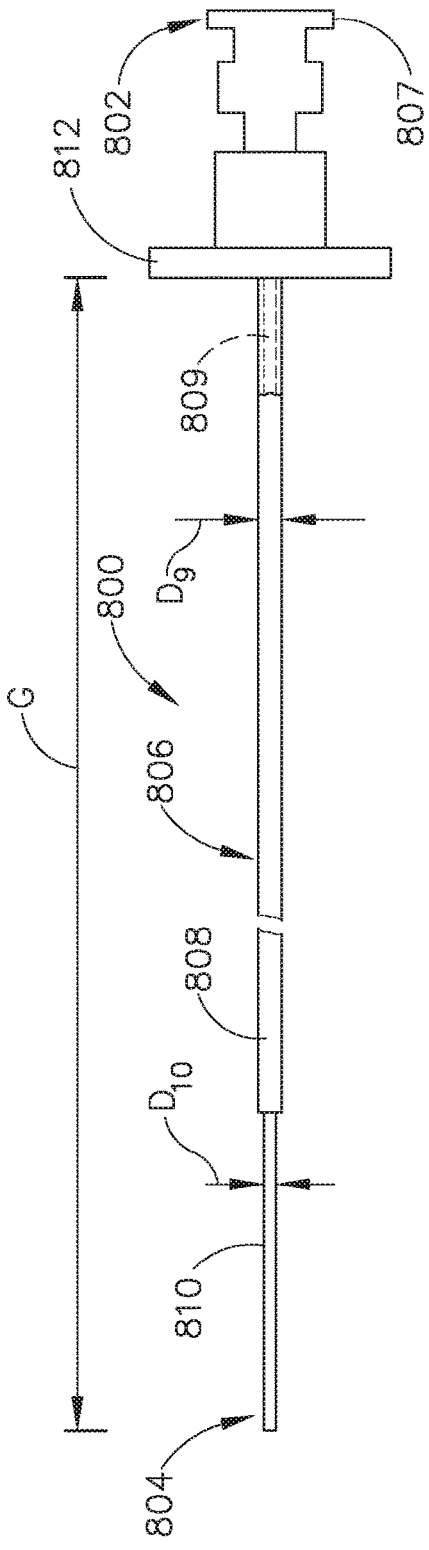
FIG. 17 depicts a side elevational view of another exemplary alternative needle that may be used with the guide catheter of FIG. 16.

FIG. 17 shows an exemplary alternative needle (800) that may be used to access and anesthetize the ET (26). Needle (800) may be guided to ET (26) using guide catheter (100, 700). In the present example, needle (800) is sized and configured specifically such that only a portion of distal end of needle (800) may protrude distally of distal end of guide catheter (700), as discussed in further detail below. Needle (400) may be fluidly coupled with a source of fluid in a syringe, for example, and directed into the ET (26) with or without a guide catheter (100, 700), to deliver an anesthetic fluid to the ET (26). It will be understood that in addition or in the alternative, needle (800) may be utilized to deliver a non-anesthetic, therapeutic fluid and/or any other suitable kinds of fluids to the ET (26).

As shown, needle (800) includes a proximal end (802), a distal end (804), and a shaft (806) extending therebetween. Needle (800) defines a lumen (809) that extends continuously along the length of shaft (806). Proximal end (802) includes a female luer component (807) that is configured to be mechanically and fluidly coupled with a source of fluid, such as a syringe, tubing, etc, such that fluid may be communicated through lumen (809) and out of distal end (804).

In the present example, a first, more proximal portion (808) of shaft (806) includes a first cross-sectional dimension ($D_9$), and a second, more distal portion (810) of shaft (806) includes a second cross-sectional dimension ($D_{10}$), providing a neck-down at distal portion (810). The first cross-sectional dimension ($D_9$) is larger than the second cross-sectional dimension ($D_{10}$), such that proximal portion (808) is relatively stiffer to provide pushability; while the distal portion (810) provides flexibility, which may prevent damage to an anatomical structure as needle (800) is advanced therethrough. Needle (800) includes sufficient flexibility in order to traverse the bend (122, 722) of guide catheter (100, 700) (or bends in the anatomy), for example, but also includes sufficient stiffness to provide pushability through guide catheter (100, 700) and/or the ET (26). In the example shown, shaft (806) and luer component (807) are made from Type 304 Stainless Steel. However, shaft (806) and luer component (807) may instead be made from any other suitable material(s) as will be understood by persons skilled in the art in view of the teachings herein.

In the present example, the first cross-sectional dimension ($D_9$) is about 0.050 inches, and the second cross-sectional dimension ($D_{10}$) is about 0.0165 inches. In the present example, needle (800) is cylindrical in shape and therefore the first and second cross-sectional dimensions ($D_9$, $D_{10}$) are outer diameters of the respective portions (808, 810) of needle (800). In the present example, the inner diameter (i.e., of lumen (809)) at the first portion (808) is about 0.028 inches. Of course, any other suitable dimensions may be used. It will be understood that where needle (800) includes a cross-sectional shape other than a circle, first and second cross-sectional dimensions (D1, D2) and inner cross sectional dimensions (i.e., of lumen (809)) may have other characteristics.

As shown in the present example, needle (800) does not include a taper between the proximal and distal portions (808, 810) and instead includes a stepped transition between proximal and distal portions (808, 810). In some other examples, needle (800) may include a tapered transition between proximal and distal portions (808, 810). As shown, needle (806) includes a stop flange (812) that is circular in cross-section and is configured to limit the distal advancement of needle (800) relative to guide catheter (700).

In the present example, guide catheter (700) and needle (800) may be directed into the oro-nasal cavity as a unit, in the manner shown in FIG. 5A, such that no portion of shaft (806) of needle (800) protrudes from distal end (706) of guide catheter (700). Once the guide catheter (700) is properly placed relative to the ET (26), for example, an operator may advance needle (800) distally relative to catheter (700) such that stop flange (812) abuts proximal end (734). In the example shown, needle (800) and guide catheter (700) are sized and configured such that when flange (812) abuts proximal end (734) of guide catheter (700), shaft (806) of needle (800) protrudes from distal end (706) of guide catheter (700) a predetermined distance y. Then, an operator may direct fluid through lumen (509) and out of distal end of shaft (506) into the ET (26), for example.

In the example shown, y=G−L, discussed above. In some examples, length G is 8 inches, but any other suitable length may be used.

D. Drug Delivery Catheter Including Distal Apertures and Flow Reducing Sponge

FIGS. 18-20 show an exemplary alternative catheter (900) that is configured to deliver therapeutic materials in a controlled and precise manner to various anatomical structures, such as the ET (26) or other regions associated with the oro-nasal cavity. Catheter (900) may be fluidly coupled with a source of fluid in a syringe, for example, and directed into the ET (26) or other anatomical structures, with or without a guide catheter (100), to deliver an anesthetic fluid. It will be understood that in addition or in the alternative, catheter (900) may be utilized to deliver a non-anesthetic, therapeutic fluid and/or other kinds of fluids. As shown, catheter (900) includes a proximal end (902), a distal end (904), and a shaft (906) extending therebetween. Catheter (900) further defines a lumen (909) that extends continuously along the length of shaft (906).

Proximal end (902) includes a female luer component (907) that is configured to be mechanically and fluidly coupled with a source of fluid, such as a syringe, tubing, etc, such that fluid may be communicated through lumen (909) toward distal end (904). As shown, shaft (906) includes uniform inner and outer cross-sectional dimensions along the entire length of shaft (906). The materials and/or material characteristics of shaft (906) may be varied in order to provide different characteristics at different portions of catheter (900). For example, similar to needles discussed above, the cross-sectional dimensions of catheter (906) along shaft (906) may be varied to provide a desired combination of rigidity (e.g., along a proximal portion of shaft (906)) and flexibility (e.g., along a distal portion of shaft (906)).

In the present example, distal end (904) includes features that prevent the fluid in lumen (909) from rapidly exiting the distal end and traveling beyond the anatomical location the operator intended. Particularly, shaft (906) includes a plurality of apertures (910) at or near the distal end (904) of shaft (906) and a flow reducing sponge (914) positioned within lumen (909), coincident with apertures (910). In the present example, distal end (904) of catheter (900) includes an opening (912) such that fluid may escape from the apertures (910) and out of distal end opening (912). However, in some examples, distal end of catheter (900) may not include an opening, such that fluid may only escape from apertures (910). As shown, apertures (910) extend through the wall of the shaft and into the lumen (909). In the present example, catheter (900) includes a longitudinally extending array of six angularly extending rows of apertures (910) about the circumference of shaft (906), with each row of apertures (910) being proximally or distally offset from an adjacent row of apertures (910). In other examples, however, there may be more or fewer apertures (910) than shown in any suitable configuration as will be apparent to persons skilled in the art in view of the teachings herein.

FIGS. 19-20 show sponge member (914) within lumen (909) at distal end (904). As shown, sponge member (914) is coincident with apertures (910) such that in order to flow out of apertures (910), fluid flowing through catheter (900) flows through sponge (914). In the present example, sponge (914) is configured to provide a level of fluid resistance to reduce the flow rate of fluid traveling through lumen (909) such that the fluid weeps or drips, and does not flow continuously, out of opening (912) and apertures (910). However, in other examples, sponge (914) may be configured to provide a level of fluid resistance to reduce the flow rate of fluid traveling through lumen (909) such that the fluid flows continuously out of apertures (910) and opening (912), but at a lower flow rate than the fluid would otherwise flow through portions of lumen (909) without sponge (914).

Sponge (909) may be made from one or both of natural or man-made materials. For example, sponge may be made from cellulose, melamine, or other suitable materials as will be apparent to persons skilled in the art in view of the teachings herein. Sponge (914) may be a woven or nonwoven matrix of material(s), or may be an open or closed cell foam structure. Additionally or alternatively, sponge (914) may be made from natural, dried or moist sponges. Other suitable configurations of sponge (914) will be apparent to persons skilled in the art in view of the teachings herein.

E. Balloon Catheters including Venting Features

Utilizing balloon catheters in the oro-nasal cavity may result in pressure accumulating in certain portions of the cavity. For example, pressure may accumulate in the middle ear (14) during an ET (26) dilation procedure. It may therefore provide comfort for patients to provide a manner of reducing and equalizing pressure in the middle ear (14), for example, during ET (26) dilation procedures. The following examples include devices that have venting features that are configured to prevent pressure accumulation in the middle ear (14) during an ET (26) treatment. The following devices are also configured to provide communication of fluid (e.g., anesthetic, therapeutic agents, etc.) to the ET (26), via the same passageway through which ventilation is provided or through a separate fluid delivery passageway.

1. Balloon Catheter Including Three Lumens

FIGS. 21A-22 show an exemplary alternative balloon dilation catheter (1200).

Balloon dilation catheter (1200) of the present example generally includes an elongate shaft (1202) having a proximal end (1214) and a distal end (1218). Balloon dilation catheter (1200) further includes a balloon (1204) on distal end (1218) of elongate shaft (1202). Balloon (1204) may be a polymer balloon (compliant, semi-compliant, or non-compliant). In some versions, balloon (1204) comprises a suitable non-compliant material such as but not limited to polyethylene terephthalate (PET), PEBAX® (polyether block amide), nylon or the like. Balloon dilation catheter (1200) may include any size of balloon including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm). Balloon dilation catheter (1200) generally includes a proximally located connection (1230) for inflating/activating the balloon (1204) by communicating a pressurized medium (e.g., saline) to balloon (1204).

Balloon dilation catheter (1200) further includes an actuator (1210). Actuator (1210) has a proximal side (1220) and a distal side (1222). In the example shown in FIG. 21A, actuator (1210) is secured by an adhesive to elongate shaft (1202). The portion (1240) of elongate shaft (1202) that is distal of actuator (1210) is sufficiently stiff to be guided through the nasal cavity and into the ET (26) and is constructed of stainless steel (e.g., a stainless steel hypotube). The portion (1238) of elongate shaft (1202) that is proximal of actuator (1210) and the portion (1250) that is distal to portion (1240) is more flexible than the portion (1240) and is constructed of a polymeric material including but not limited to PEBAX® (polyether block amide). In this way, proximal portion (1238) of elongate shaft (1202) will not interfere with the endoscope (60) described above as it is advanced through the nasal passage, such that dilation catheter (1200) can be easily viewed. Actuator (1210) allows for easy, ergonomic one-handed advancement of dilation catheter (1200) through guide catheter (100) and into the ET (26). Actuator (1210) may be used to advance or retract in alternative ways including but not limited to use of the thumb, the index finger, or a combination of fingers (e.g., the index and middle fingers) or the thumb and the index or middle finger.

The distal end (1218) of balloon catheter (1200) further includes a tip (1212) and a flexible shaft portion (1250) that is constructed of a polymeric material including but not limited to PEBAX® (polyether block amide) that extends from the distal end of the elongate shaft (1202) to the proximal end of balloon (1204). In the example shown in FIG. 21A, tip (1212) is a bulbous polymeric blueberry shaped, atraumatic tip and is about 1.5 mm to about 2 mm in length, with an outer diameter of between about 2 mm and about 3 mm. The smoothness and roundness of tip (1212) facilitates advancement of balloon catheter (1200) by helping it glide smoothly through the ET (26). Tip (1212) further acts as a safety stop. The isthmus (29) of the ET (26), shown in FIG. 1 is approximately 1 mm in diameter. Tip (1212) diameter is larger than the outer diameter (1233) of the elongate shaft (1202), shown in cross-section in FIG. 21B, such that tip (1212) size will prevent the balloon catheter (1200) from passing through the isthmus (29) into the middle ear (14).

Balloon (1204) may be expanded to dilate the ET (26) after balloon (1204) is placed in a desirable location in the ET (26). For example, the opening area of the ET (26) includes a pharyngeal ostium (28), and dilation catheter (1200) may be advanced to position balloon (1204) in the pharyngeal ostium (28). An endoscope, such as endoscope (60) (FIGS. 8-9), may be used to assist in positioning the dilation catheter (1200). Endoscope (60) may be advanced through the nasal passage to view dilation catheter (1200). A marker (1208) on a shaft of the dilation catheter (1200) can be viewed from endoscope (60) to approximate a location of balloon (1204) relative to the opening of the ET (26) (e.g., pharyngeal ostium (28)) based on a distance of marker (1208) from a proximal end of balloon (1204). Accordingly, dilation catheter (1200) can be moved to place marker (1208) in a desirable location before expansion of balloon (1204) in the ET (26).

Balloon (1204) may be held in location while in an expanded state for an extended period of time (e.g. several seconds or minutes). Balloon dilation catheter (1200) may also deliver a substance to the ET (26), such as one or more of the therapeutic or diagnostic agents described herein. Balloon (1204) may also carry an expandable stent for delivery into the ET (26) upon expansion of balloon (1204). Balloon dilation catheter (1200) and guide catheter (100) may be removed from the patient after balloon (1204) has been deflated/unexpanded. The ET (26) will resume functioning, normally opening and closing to equalize atmospheric pressure in the middle ear (14) and protect the middle ear (14) from unwanted pressure fluctuations and loud sounds.

In the present example, elongate shaft (1202) contains adjacent triple lumen (1232, 1234, 1236) tubing (see FIG. 21B). By adjacent triple lumen tubing, it is intended that the lumens (1232, 1234, 1236) are next to each other but are spaced apart, one from the other. The inflation lumen (1232) is used for inflation of balloon (1204) with water, contrast medium, or saline through inflation port (1230) to a pressure of between about 3 and about 15 atmospheres, or of between about 6 and about 12 atmospheres.

Injection lumen (234) permits the optional injection of anesthetic, a therapeutic agent, some other fluid, or even the introduction of a guidewire (80) or any of the needles described herein, through the injection port (1237) at the proximal end (1216) of the proximal connector (1206). It should therefore be understood that injection lumen (234) may be used to deliver fluid to the ET (26) while ventilation lumen (1236) provides ventilation to the ET (26). As yet another merely illustrative variation, ventilation lumen (1236) may be used to communicate fluid (e.g., an anesthetic, a therapeutic agent, and/or some other fluid) to the ET (26) after ventilation lumen (1236) has provided ventilation to the ET (26).

In order to ensure that inflation port (1230) is used for balloon (1204) inflation only, inflation port (1230) and injection port (1237) may optionally have different type connectors. For example, inflation port (1230) may be a female connector whereas injection port (1237) is a male connector or vice versa. Alternatively, injection port (1237) may have a right-handed thread connector and inflation port (1230) may have a left-handed thread connector or vice versa.

Ventilation lumen (1236) extends from a lateral opening (1239) in shaft (1202) that is distal to the distal bond of balloon (1204), along the length of shaft (1202), and proximally terminates at lateral ventilation port (1238). Therefore, fluids (air, liquids) may travel through lateral opening (1239), along ventilation lumen (1236), and out of port (1238) to equalize pressure in an area that is positioned distal to balloon (1204). For example, when balloon catheter (1200) is utilized in an ET dilation procedure such as that shown in FIGS. 10A-10C, ventilation lumen (1236) may assist in equalizing pressure in middle ear (14) during the inflation of balloon (1204).

2. Balloon Dilation Catheter with Ventilation Lumen Extending Along Balloon Length FIGS. 23A-23C show another exemplary alternative balloon catheter (1300). Balloon catheter (1300) is substantially identical to balloon catheter (200) in several respects. For instance, balloon catheter (1300) includes an alternative shaft (1302) including inflation lumen (232) and injection lumen (234) that are configured in accordance with lumens (232, 234) of balloon catheter (200). However, unlike balloon catheter (200), balloon catheter (1300) of this example includes a ventilation lumen (1336) extending along the length of the balloon (204). As shown in the present example, a first, proximal end (1338) of ventilation lumen (1336) terminates distal to the proximal balloon bond, and a second, distal end (1340) terminates proximal to tip (212) but distal to balloon (204). Therefore, fluids (air, liquids) may travel through second end (1340) of ventilation lumen (1336) and out of first end (1338) to equalize pressure in an area that is positioned distal to balloon (204). For example, when balloon catheter (1300) is utilized in an ET (26) dilation procedure such as that shown in FIGS. 10A-10C, ventilation lumen (1336) may assist in equalizing pressure in middle ear (14) during the inflation of balloon (204), due to the position of first end (1338) being located proximal to balloon (204).

Injection lumen (234) permits the optional injection of anesthetic, a therapeutic agent, some other fluid, or even the introduction of a guidewire (80) or any of the needles described herein, through an injection port at the proximal end of balloon catheter (1300). It should therefore be understood that injection lumen (234) may be used to deliver fluid to the ET (26) while ventilation lumen (1336) provides ventilation to the ET (26).

3. Balloon Dilation Catheter with Ventilation Lumen Extending Along Balloon Length and Including Apertures in Shaft FIGS. 24A-24C show another exemplary alternative balloon catheter (1400). Balloon catheter (1400) is substantially identical to balloon catheter (200) in several respects. For instance, balloon catheter (1400) includes an alternative shaft (1402) including inflation lumen (232) and injection lumen (234) that are configured in accordance with lumens (232, 234) of balloon catheter (200). However, unlike balloon catheter (200), balloon catheter (1400) of this example includes a ventilation lumen (1436) extending along the length of the balloon (204). As shown in the present example, a first, proximal end (1438) of ventilation lumen (1436) terminates distal to the proximal balloon end, and a second, distal end (1440) terminates proximal to tip (212) but distal to balloon (204).

In the present example, ventilation lumen (1436) includes a plurality of lateral apertures (1442) near the first end (1438). Therefore, fluids (air, liquids) may travel through second end (1440) of ventilation lumen (1436) and out of first end (1438) and apertures (1442) to equalize pressure in an area that is positioned distal to balloon (204). For example, when balloon catheter (1400) is utilized in an ET dilation procedure such as that shown in FIGS. 10A-10C, ventilation lumen (1436) may assist in equalizing pressure in middle ear (14) during the inflation of balloon (204), due to the position of first end (1338) being located proximal to balloon (204).

Injection lumen (234) permits the optional injection of anesthetic, a therapeutic agent, some other fluid, or even the introduction of a guidewire (80) or any of the needles described herein, through an injection port at the proximal end of balloon catheter (1400). It should therefore be understood that injection lumen (234) may be used to deliver fluid to the ET (26) while ventilation lumen (1436) provides ventilation to the ET (26).

4. Balloon Dilation Catheter with Enlarged Ventilation and Injection Lumen

FIGS. 25A-25B show another exemplary alternative balloon catheter (1500). Balloon catheter (1500) is substantially similar to balloon catheter (200), except that balloon catheter (1500) includes ventilation, injection, and inflation features, discussed in more detail below. Balloon dilation catheter (1500) of the present example generally includes an elongate shaft (1502) having a proximal end (1514) and a distal end (1518). Balloon dilation catheter (1500) further includes a balloon (1504) on distal end (1518) of elongate shaft (1502). Balloon (1504) may be a polymer balloon (compliant, semi-compliant, or non-compliant). In some versions, balloon (1504) comprises a suitable non-compliant material such as but not limited to polyethylene terephthalate (PET), PEBAX® (polyether block amide), nylon, or the like. Balloon catheter (1500) may include any size of balloon including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm). Balloon dilation catheter (1500) generally includes a proximally located connection (1530) for inflating/activating the balloon (1504) by communicating a pressurized medium (e.g., saline) to balloon (1504).

Balloon dilation catheter (1500) further includes an actuator (1510). Actuator (1510) has a proximal side (1520) and a distal side (1522). In the example shown in FIG. 25A, actuator (1510) is secured by an adhesive to elongate shaft (1502). The portion (1540) of elongate shaft (1502) that is distal of actuator (1510) is sufficiently stiff to be guided through the nasal cavity and into the ET (26) and is constructed of stainless steel (e.g., a stainless steel hypotube). The portion (1538) of elongate shaft (1502) that is proximal of actuator (1510) and the portion (1550) that is distal to portion (1540) is more flexible than the portion (1540) and is constructed of a polymeric material including but not limited to PEBAX® (polyether block amide). In this way, proximal portion (1538) of elongate shaft (1502) will not interfere with endoscope (60) described above as it is advanced through the nasal passage, such that dilation catheter (1500) can be easily viewed. Actuator (1510) allows for easy, ergonomic one-handed advancement of dilation catheter (1500) through guide catheter (100) and into the ET (26). Actuator (1510) may be used to advance or retract in alternative ways including but not limited to use of the thumb, the index finger, or a combination of fingers (e.g., the index and middle fingers) or the thumb and the index or middle finger.

Distal end (1518) of balloon catheter (1500) further includes a tip (1512) and a flexible shaft portion (1550) that is constructed of a polymeric material including but not limited to PEBAX® (polyether block amide) that extends from the distal end of the elongate shaft (1502) to the proximal end of balloon (1504). In the present example, tip (1512) is a bulbous polymeric blueberry shaped, atraumatic tip and is about 1.5 mm to about 2 mm in length, with an outer diameter of between about 2 mm and about 3 mm. The smoothness and roundness of tip (1512) facilitates advancement of balloon catheter (1500) by helping it glide smoothly through the ET (26). Tip (1512) further acts as a safety stop. The isthmus (29) of the ET (26), shown in FIG. 1 is approximately 1 mm in diameter. Tip (1512) diameter is larger than the outer diameter (1533) of elongate shaft (1502) such that tip (1512) size will prevent balloon catheter (1500) from passing through the isthmus (29) into the middle ear (14).

Balloon (1504) may be expanded to dilate the ET (26) after balloon (1504) is placed in a desirable location in the ET (26). For example, the opening area of the ET (26) includes a pharyngeal ostium (28), and dilation catheter (1500) may be advanced to position the balloon in the pharyngeal ostium (28). An endoscope, such as endoscope (60) (FIGS. 8-9), may be used to assist in positioning dilation catheter (1500). Endoscope (60) may be advanced through the nasal passage to view dilation catheter (1500). A marker (1508) shaft (1502) of dilation catheter (1500) can be viewed from endoscope (60) to approximate a location of balloon (1504) relative to the opening of the ET (26) (e.g., pharyngeal ostium (28)) based on a distance of marker (1508) from a proximal end of the balloon (1504). Accordingly, dilation catheter (1500) can be moved to place marker (1508) in a desirable location before expansion of balloon (1504) in the ET (26).

In the present example, elongate shaft (1502) contains adjacent dual lumen (1532, 1534) tubing. By adjacent dual lumen tubing, it is intended that the lumens (1532, 1534) are next to each other but are spaced apart, one from the other, as shown in FIG. 25B. As shown in FIG. 25A, balloon catheter (1500) includes a proximal hub (1506) that is similar to hub (206), except for that inflation port (1530) includes an elongate tube (1540) extending proximally from hub (1506). Elongate tube (1540) includes a first portion (1542) extending at an oblique angle ($\theta_3$) relative to the longitudinal axis of balloon catheter (1500) and a second portion (1544) extending parallel to the longitudinal axis of balloon catheter (1500). Inflation tube (1530) further includes a female luer (1546) at the end of tube (1530) adjacent to second portion (1544).

Inflation lumen (1532) is used for inflation of the balloon (1504) with water, contrast medium, or saline through inflation port (1530) to a pressure of between about 3 and about 15 atmospheres, or of between about 6 and about 12 atmospheres. Inflation lumen extends from the distal most portion of first portion (1542) of tube (1540) and terminates at an opening on shaft (1502) within balloon (1504).

Injection lumen (1534) extends from port (1536) and through the entire length of shaft (1502) and terminates at an opening in tip (1512). Lumen (1534) permits the injection of water, medicament, or even the introduction of a guidewire (80) or any of the needles described herein, through the injection port 1536 at the proximal end (1516) of the proximal hub (1506). Lumen (1534) is sized and configured such that such that there is open space for ventilation through lumen (1534) even when the lumen is occupied with a guidewire (80) or any of the needles described herein. In the present example, lumen (1534) is sized to remain fully open if the guidewire (80), needle, or other inserted instrument is not extended distally; and will stay open, but with less luminal space when the guidewire (80), needle, or other inserted instrument is extended distally within lumen (1534).

Due to the configuration of lumen (1534), fluids (air, liquids) may travel through tip (1512) into lumen and out of port (1536). For example, when balloon catheter (1500) is utilized in an ET (26) dilation procedure such as that shown in FIGS. 10A-10C, lumen (1534) may assist in equalizing pressure in middle ear (14) during the inflation of balloon (1504), due to the position of port (1536) being located proximal to balloon (1504). Lumen (1534) may thus be used to communicate fluid (e.g., an anesthetic, a therapeutic agent, and/or some other fluid) to the ET (26) in addition to providing ventilation to the ET (26).

Balloon (1504) may be held in location while in an expanded state for an extended period of time (e.g. several seconds or minutes). Balloon catheter (1500) may also deliver a substance to the ET (26), such as one or more of the therapeutic or diagnostic agents described herein. Balloon (1504) may also carry an expandable stent for delivery into the ET (26) upon expansion of balloon (1504). Balloon dilation catheter (1500) and guide catheter (100) may be removed from the patient after balloon (1504) has been deflated/unexpanded. The ET (26) will resume functioning, normally opening and closing to equalize atmospheric pressure in the middle ear (14) and protect the middle ear (14) from unwanted pressure fluctuations and loud sounds.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for delivering a fluid to a Eustachian tube (ET) of a patient, the system comprising: (a) a guide member, wherein the guide member comprises a shaft having a proximal portion and a distal portion, wherein the guide member further comprises a bend at the distal portion, wherein the bend is configured to provide access to an opening in the ET; and (b) a tubular member comprising a proximal end, a distal end, and a lumen extending therebetween, wherein the tubular member is sized to fit within the ET, wherein one or both of the tubular member and guide member comprises a first stop member configured to engage the other of the tubular member or the guide member, wherein the first stop member is configured to restrict a distal advancement of the tubular member relative to the guide member.

Example 2

The system of Example 1, wherein the tubular member comprises a proximal portion and a distal portion, wherein the proximal portion is stiffer than the distal portion.

Example 3

The system of any one or more of Examples 1 through 2, wherein the tubular member comprises a proximal portion having a first cross-sectional dimension and a distal portion comprising a second cross-sectional dimension, wherein the first cross-sectional dimension is greater than the second cross-sectional dimension.

Example 4

The system of Example 3, wherein the first cross sectional dimension is between about 0.30 inches and about 0.060 inches, wherein the second cross-sectional dimension is between about 0.015 inches and about 0.040 inches.

Example 5

The system of any one or more of Examples 1 through 4, wherein the first stop member is configured to prevent the distal end of the tubular member from extending past the distal portion of the guide member a predetermined amount.

Example 6

The system of Example 5, wherein the predetermined amount comprises between about 5 mm and about 25 mm.

Example 7

The system of any one or more of Examples 1 through 6, wherein the stop member comprises a flange on the tubular member.

Example 8

The system of any one or more of Examples 1 through 7, wherein the stop member comprises a proximal portion of the guide catheter.

Example 9

The system of any one or more of Examples 1 through 8, further comprising a sheath, wherein the tubular member is configured to be inserted into the sheath and the sheath is configured to be inserted into the guide member.

Example 10

The system of Example 9, wherein the sheath is configured to lockingly receive the proximal portion of the guide member to prevent relative movement between the sheath and the guide member.

Example 11

The system of any one or more of Examples 9 through 10, further comprising a second stop member, wherein the second stop member is disposed on the sheath.

Example 12

The system of any one or more of Examples 9 through 11, wherein the sheath includes a hub including a recess, wherein the recess is configured to receive the proximal portion of the guide member.

Example 13

The system of any one or more of Examples 1 through 12, wherein the tubular member comprises a preformed bend at or near the distal end.

Example 14

The system of any one or more of Examples 1 through 13, wherein the shaft of the guide member consists essentially of stainless steel.

Example 15

The system of any one or more of Examples 1 through 14, wherein the tubular member comprises a plurality of apertures at or near the distal end, wherein the tubular member comprises a flow limiting member disposed in the lumen, wherein the flow limiting coincident with at least a portion of the apertures.

Example 16

The system of Example 15, wherein the flow limiting element comprises a sponge member.

Example 17

A method of treating a Eustachian tube (ET) of a patient using a guide member and a tubular member, wherein one or both of the guide member and tubular member comprises a stop member configured to limit a restrict advancement of the tubular member relative to the guide member, wherein the method comprises: (a) directing the guide member into an oro-nasal cavity of the patient; (b) directing the tubular catheter into the oro-nasal cavity of the patient; (c) advancing at least part of a distal portion of the guide member adjacent to or into an opening of the ET; (d) advancing the tubular member relative to the guide member such that a distal end of the tubular member is positioned coincident with at least a portion of the ET; and (e) directing a fluid through the tubular member and out of the tubular member and onto at least a portion of the ET.

Example 18

The method of Example 17, wherein the fluid comprises an anesthetic.

Example 19

A method of treating a Eustachian tube (ET) of a patient using a guide member and a dilation catheter, wherein the method comprises: (a) directing the guide member into an oro-nasal cavity of the patient; (b) directing the dilation catheter into the oro-nasal cavity of the patient; (c) advancing at least part of a distal portion of the guide member into an opening of the ET; (d) advancing the dilation catheter relative to the guide member such that an expandable element of the dilation catheter is positioned distal to a distal end of the guide member; (e) expanding the expandable member to thereby dilate the ET; (f) venting the anatomical structures that are positioned distal to the expandable member; and (g) delivering a fluid to the ET.

Example 20

The method of Example 19, wherein the dilation catheter comprises a ventilation lumen including a first opening positioned distal to the expandable element and a second opening positioned proximal to the expandable element.

VI. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for delivering a fluid to a Eustachian tube (ET) of a patient, the system comprising:
    (a) a guide member that includes a shaft, wherein the shaft includes a proximal portion, a distal portion, and a lumen extending therebetween; and
    (b) a tubular member that is sized to fit within the ET, wherein the tubular member is configured to be positioned within the lumen of the guide member, wherein the tubular member comprises:
        (i) opposing proximal and distal ends,
        (ii) a lumen extending between the proximal and distal ends,
        (iii) a plurality of lateral apertures disposed adjacent the distal end, and
        (iv) a flow limiting member disposed within the lumen of the tubular member, wherein the flow limiting member includes a body configured to reduce a flow rate of the fluid traveling through the flow limiting member and out of the plurality of lateral apertures to the ET.

2. The system of claim 1, wherein the flow limiting member is coincident with at least a portion of the plurality of lateral apertures.

3. The system of claim 2, wherein the flow limiting element comprises a sponge member.

4. The system of claim 3, wherein the sponge member is formed from cellulose or melamine.

5. The system of claim 1, wherein the distal end of the tubular member includes an opening such that the fluid is configured to escape from both of the plurality of lateral apertures and the opening to the ET.

6. The system of claim 5, wherein the sponge member is configured to provide a level of fluid resistance to reduce the flow rate of the fluid traveling through the lumen of the tubular member such that the fluid weeps or drips, and does not flow continuously out of the opening to the ET.

7. The system of claim 1, wherein the distal end of the tubular member does not include an opening, such that the fluid is configured to only escape from the plurality of apertures.

8. The system of claim 1, wherein the plurality of lateral apertures form a longitudinally extending array of angularly extending rows of apertures about the circumference of tubular member.

9. The system of claim 8, wherein each angularly extending row of apertures is proximally or distally offset from an adjacent angularly extending row of apertures.

10. The system of claim 1, wherein the guide member further comprises a bend at the distal portion, wherein the bend is configured to provide access to an opening in the ET, wherein the guide member, including the shaft and the bend, is rigid.

11. The system of claim 1, wherein one or both of the tubular member and guide member comprises a first stop member configured to engage the other of the tubular member or the guide member, wherein the first stop member is configured to restrict a distal advancement of the tubular member relative to the guide member.

12. The system of claim 1, wherein the fluid is configured to not flow continuously out of the distal end and the plurality of lateral apertures to the ET.

13. The system of claim 1, wherein the fluid is configured to flow continuously out of the plurality of lateral apertures to the ET using the flow limiting member but at the reduced rate than the fluid would flow to the ET without the flow limiting member.

14. The system of claim 1, further comprising a fluid supply containing the fluid in fluid communication with the lumen, wherein the fluid includes an anesthetic fluid configured to anesthetize the ET.

15. A system for delivering a fluid to a Eustachian tube (ET) of a patient, the system comprising:
(a) a guide member that includes a shaft, wherein the shaft includes a proximal portion, a distal portion, and a lumen extending therebetween; and
(b) a tubular member that is sized to fit within the ET, wherein the tubular member is configured to be positioned within the lumen of the guide member, wherein the tubular member comprises:
(i) opposing proximal and distal ends,
(ii) a lumen extending between the proximal and distal ends,
(iii) a plurality of lateral apertures disposed adjacent the distal end, and
(iv) a flow limiting member disposed within the lumen of the tubular member, wherein the fluid is configured to flow through the flow limiting member and out of the plurality of lateral apertures to the ET.

16. The system of claim 15, wherein the fluid is configured to not flow continuously out of the distal end and the plurality of lateral apertures to the ET.

17. The system of claim 15, wherein the flow limiting member is configured to prevent the fluid from rapidly exiting through the plurality of lateral apertures distal end and traveling beyond the ET.

18. A system for delivering a fluid to a Eustachian tube (ET) of a patient, the system comprising:
(a) a guide member that includes a shaft, wherein the shaft includes a proximal portion, a distal portion, and a lumen extending therebetween; and
(b) a tubular member that is sized to fit within the ET, wherein the tubular member is configured to be positioned within the lumen of the guide member, wherein the tubular member comprises:
(i) opposing proximal and distal ends,
(ii) a lumen extending between the proximal and distal ends,
(iii) a plurality of lateral apertures disposed adjacent the distal end, and
(iv) a sponge member disposed within the lumen of the tubular member, wherein the fluid is configured to flow through the sponge member and out of the tubular member through the plurality of lateral apertures to the ET.

19. The system of claim 18, wherein the sponge member is configured to prevent the fluid from flowing continuously out of the plurality of lateral apertures to the ET.

20. The system of claim 18, wherein the distal end of the tubular member includes an opening such that the fluid is configured to escape from both of the plurality of lateral apertures and the opening to the ET.

* * * * *